(12) United States Patent
Kintz et al.

(10) Patent No.: US 10,045,722 B2
(45) Date of Patent: Aug. 14, 2018

(54) METHOD AND DEVICE FOR CORRECTING OPTICAL SIGNALS

(71) Applicant: Profusa, Inc., South San Francisco, CA (US)

(72) Inventors: Gregory J. Kintz, Santa Cruz, CA (US); William McMillan, La Honda, CA (US); Natalie Wisniewski, San Francisco, CA (US)

(73) Assignee: Profusa, Inc., South San Francisco, CA (US)

( * ) Notice: Subject to any disclaimer, the term of this patent is extended or adjusted under 35 U.S.C. 154(b) by 0 days.

(21) Appl. No.: 14/199,497

(22) Filed: Mar. 6, 2014

(65) Prior Publication Data

US 2014/0275869 A1     Sep. 18, 2014

Related U.S. Application Data

(60) Provisional application No. 61/785,087, filed on Mar. 14, 2013.

(51) Int. Cl.
*A61B 5/00* (2006.01)
*A61B 5/1459* (2006.01)
*A61B 5/145* (2006.01)

(52) U.S. Cl.
CPC ........ *A61B 5/1459* (2013.01); *A61B 5/14532* (2013.01); *A61B 5/7203* (2013.01)

(58) Field of Classification Search
CPC .............. A61B 5/14546; A61B 5/1453; A61B 5/14503
See application file for complete search history.

(56) References Cited

U.S. PATENT DOCUMENTS

| 4,703,756 A | 11/1987 | Gough et al. |
|---|---|---|
| 5,242,835 A | 9/1993 | Jensen |

(Continued)

FOREIGN PATENT DOCUMENTS

| CN | 1675547 A | 9/2005 |
|---|---|---|
| CN | 1882278 A | 12/2006 |

(Continued)

OTHER PUBLICATIONS

HyperSpectral imaging microscopy for identification and quantitative analysis of fluorescently-labeled cells in highly autfluorescent tissue, S. Leavesley, N. Annamdevula, J. Boni, S. Stocker, K. Grant, B. Troyanovsky, T. C. Rich, D. F. Alvarez, J Biophotonics, 5(1), pp. 67-48, 2012.*

(Continued)

*Primary Examiner* — Tse Chen
*Assistant Examiner* — Joanne Hoffman

(57) ABSTRACT

An optical device is used to monitor an implant embedded in the tissue of a mammal (e.g., under the skin). The implant receives excitation light from the optical device and emits light that is detected by the optical device, including an analyte-dependent optical signal. Scatter and absorption properties of tissue change over time due to changes in hydration, blood perfusion and oxygenation. The optical device has an arrangement of light sources, filters and detectors to transmit excitation light within excitation wavelength ranges and to measure emitted light within detection wavelengths. Changes in scattering and absorption of light in the tissue, such as diffuse reflectance, are monitored. The light sources, filters and detectors may also be used to monitor autofluorescence in the tissue to correct autofluorescence background.

29 Claims, 8 Drawing Sheets

(56) References Cited

U.S. PATENT DOCUMENTS

| | | | |
|---|---|---|---|
| 5,284,140 A | 2/1994 | Allen et al. | |
| 5,371,122 A | 12/1994 | Kawahara et al. | |
| 5,487,885 A | 1/1996 | Sovak et al. | |
| 5,551,422 A | 9/1996 | Simonsen et al. | |
| 5,777,060 A | 7/1998 | Van Antwerp | |
| 5,837,865 A | 11/1998 | Vinogradov et al. | |
| 5,895,658 A | 4/1999 | Fossel | |
| 5,962,852 A | 10/1999 | Knuettel et al. | |
| 6,002,954 A | 12/1999 | Van Antwerp et al. | |
| 6,011,984 A | 1/2000 | Van Antwerp et al. | |
| 6,013,122 A | 1/2000 | Klitzman et al. | |
| 6,040,194 A | 3/2000 | Chick et al. | |
| 6,104,945 A | 8/2000 | Modell et al. | |
| 6,175,752 B1 | 1/2001 | Say et al. | |
| 6,212,416 B1 | 4/2001 | Ward et al. | |
| 6,274,086 B1 | 8/2001 | Wilson et al. | |
| 6,299,604 B1 | 10/2001 | Ragheb et al. | |
| 6,319,540 B1 | 11/2001 | Van Antwerp et al. | |
| 6,362,175 B1 | 3/2002 | Vinogradov et al. | |
| 6,475,750 B1 | 11/2002 | Han et al. | |
| 6,497,729 B1 | 12/2002 | Moussy et al. | |
| 6,565,509 B1 | 5/2003 | Say et al. | |
| 6,565,960 B2 | 5/2003 | Koob et al. | |
| 6,602,678 B2 | 8/2003 | Kwon et al. | |
| 6,642,015 B2 | 11/2003 | Vachon et al. | |
| 6,671,527 B2 | 12/2003 | Petersson et al. | |
| 6,702,857 B2 | 3/2004 | Brauker et al. | |
| 6,750,311 B1 | 6/2004 | Van Antwerp et al. | |
| 6,766,183 B2 | 7/2004 | Walsh et al. | |
| 6,794,195 B2 | 9/2004 | Colvin, Jr. | |
| 6,804,544 B2 * | 10/2004 | Van Antwerp | A61B 5/14532 600/310 |
| 6,818,226 B2 | 11/2004 | Reed et al. | |
| 6,821,530 B2 | 11/2004 | Koob et al. | |
| 6,844,023 B2 | 1/2005 | Schulman et al. | |
| 6,965,791 B1 | 11/2005 | Hitchcock et al. | |
| 6,994,691 B2 | 2/2006 | Ejlersen | |
| 7,060,503 B2 | 6/2006 | Colvin, Jr. | |
| 7,067,194 B2 | 6/2006 | Mao et al. | |
| 7,110,803 B2 | 9/2006 | Shults et al. | |
| 7,132,049 B2 | 11/2006 | Hou et al. | |
| 7,134,999 B2 | 11/2006 | Brauker et al. | |
| 7,153,265 B2 | 12/2006 | Vachon | |
| 7,162,289 B2 | 1/2007 | Shah et al. | |
| 7,186,789 B2 | 3/2007 | Hossainy et al. | |
| 7,192,450 B2 | 3/2007 | Brauker et al. | |
| 7,202,947 B2 * | 4/2007 | Liu et al. | 356/317 |
| 7,226,978 B2 | 6/2007 | Tapsak et al. | |
| 7,228,159 B2 | 6/2007 | Petersson et al. | |
| 7,406,345 B2 | 7/2008 | Muller et al. | |
| 7,424,317 B2 | 9/2008 | Parker et al. | |
| 7,450,980 B2 | 11/2008 | Kawanishi | |
| 7,496,392 B2 * | 2/2009 | Alarcon | G01N 21/7703 600/310 |
| 7,541,598 B2 | 6/2009 | Aasmul | |
| 7,567,347 B2 | 7/2009 | Aasmul | |
| 7,653,424 B2 | 1/2010 | March | |
| 7,772,286 B2 | 8/2010 | Muller et al. | |
| 7,869,853 B1 | 1/2011 | Say et al. | |
| 7,927,519 B2 | 4/2011 | Domschke et al. | |
| 7,939,332 B2 | 5/2011 | Colvin, Jr. | |
| 7,972,628 B2 | 7/2011 | Ratner et al. | |
| 7,972,875 B2 | 7/2011 | Rogers et al. | |
| 8,057,041 B2 | 11/2011 | Muller et al. | |
| 8,131,333 B2 | 3/2012 | Chapoy et al. | |
| 8,229,536 B2 | 7/2012 | Goode, Jr. et al. | |
| 8,249,684 B2 | 8/2012 | Kamath et al. | |
| 8,260,393 B2 | 9/2012 | Kamath et al. | |
| 8,280,476 B2 | 10/2012 | Jina | |
| 8,282,550 B2 | 10/2012 | Rasdal et al. | |
| 8,292,810 B2 | 10/2012 | Goode, Jr. et al. | |
| 8,318,193 B2 | 11/2012 | Ratner et al. | |
| 8,346,337 B2 | 1/2013 | Heller et al. | |
| 8,346,338 B2 | 1/2013 | Goode, Jr. et al. | |
| 8,346,363 B2 | 1/2013 | Darvish et al. | |
| 8,368,556 B2 | 2/2013 | Sicurello et al. | |
| 8,372,423 B2 | 2/2013 | Marshall et al. | |
| 8,385,998 B2 | 2/2013 | Zhang et al. | |
| 8,386,004 B2 | 2/2013 | Kamath et al. | |
| 8,412,301 B2 | 4/2013 | Goode, Jr. et al. | |
| 8,423,114 B2 | 4/2013 | Simpson et al. | |
| 8,428,678 B2 | 4/2013 | Kamath et al. | |
| 8,435,179 B2 | 5/2013 | Goode, Jr. et al. | |
| 8,452,361 B2 | 5/2013 | Muller | |
| 8,452,363 B2 | 5/2013 | Muller et al. | |
| 8,460,231 B2 | 6/2013 | Brauker et al. | |
| 8,465,425 B2 | 6/2013 | Heller et al. | |
| 8,483,793 B2 | 7/2013 | Simpson et al. | |
| 8,491,474 B2 | 7/2013 | Goode, Jr. et al. | |
| 8,527,025 B1 | 9/2013 | Shults et al. | |
| 8,527,026 B2 | 9/2013 | Shults et al. | |
| 8,535,262 B2 | 9/2013 | Markle et al. | |
| 8,543,182 B2 | 9/2013 | Botvinick et al. | |
| 8,543,184 B2 | 9/2013 | Boock et al. | |
| 8,543,354 B2 | 9/2013 | Luo et al. | |
| 8,562,558 B2 | 10/2013 | Kamath et al. | |
| 8,579,879 B2 | 11/2013 | Palerm et al. | |
| 8,608,924 B2 | 12/2013 | Cooper et al. | |
| RE44,695 E | 1/2014 | Simpson et al. | |
| 8,622,903 B2 | 1/2014 | Jin et al. | |
| 8,628,471 B2 | 1/2014 | Mazar et al. | |
| 8,647,271 B2 | 2/2014 | Muller et al. | |
| 8,647,393 B2 | 2/2014 | Marshall et al. | |
| 8,666,471 B2 | 3/2014 | Rogers | |
| 9,244,064 B2 | 1/2016 | Muller et al. | |
| 9,650,566 B2 | 5/2017 | Gamsey et al. | |
| 9,826,926 B2 | 11/2017 | Muller et al. | |
| 2002/0043651 A1 | 4/2002 | Darrow et al. | |
| 2002/0048577 A1 | 4/2002 | Bornstein | |
| 2002/0094526 A1 | 7/2002 | Bayley et al. | |
| 2002/0193672 A1 * | 12/2002 | Walsh | A61B 5/14532 600/316 |
| 2003/0004554 A1 | 1/2003 | Riff et al. | |
| 2003/0050542 A1 | 3/2003 | Reihl et al. | |
| 2003/0088682 A1 | 5/2003 | Hlasny | |
| 2003/0099682 A1 | 5/2003 | Moussy et al. | |
| 2003/0171666 A1 | 9/2003 | Loeb et al. | |
| 2003/0208166 A1 | 11/2003 | Schwartz | |
| 2004/0106951 A1 | 6/2004 | Edman et al. | |
| 2004/0143221 A1 | 7/2004 | Shadduck | |
| 2004/0161853 A1 | 8/2004 | Yang et al. | |
| 2004/0176669 A1 | 9/2004 | Colvin, Jr. | |
| 2004/0195528 A1 | 10/2004 | Reece et al. | |
| 2001/0259270 A1 | 12/2004 | Wolf | |
| 2004/0258732 A1 | 12/2004 | Shikinami | |
| 2004/0259270 A1 | 12/2004 | Wolf | |
| 2005/0027175 A1 | 2/2005 | Yang | |
| 2005/0095174 A1 | 5/2005 | Wolf | |
| 2005/0096587 A1 | 5/2005 | Santini, Jr. et al. | |
| 2005/0118726 A1 | 6/2005 | Schultz et al. | |
| 2005/0119737 A1 | 6/2005 | Bene et al. | |
| 2005/0154374 A1 | 7/2005 | Hunter et al. | |
| 2005/0182389 A1 | 8/2005 | LaPorte et al. | |
| 2005/0237518 A1 | 10/2005 | Colvin, Jr. et al. | |
| 2005/0245799 A1 | 11/2005 | Brauker et al. | |
| 2006/0002890 A1 | 1/2006 | Hersel et al. | |
| 2006/0002969 A1 | 1/2006 | Kyriakides et al. | |
| 2006/0089548 A1 * | 4/2006 | Hogan | 600/316 |
| 2006/0148983 A1 | 7/2006 | Muller et al. | |
| 2006/0155179 A1 | 7/2006 | Muller et al. | |
| 2006/0252976 A1 | 11/2006 | Rosero | |
| 2006/0270919 A1 * | 11/2006 | Brenner | A61B 5/14532 600/310 |
| 2006/0275340 A1 | 12/2006 | Udipi et al. | |
| 2006/0289307 A1 | 12/2006 | Yu et al. | |
| 2007/0002470 A1 | 1/2007 | Domschke et al. | |
| 2007/0004046 A1 | 1/2007 | Abbott | |
| 2007/0010702 A1 | 1/2007 | Wang et al. | |
| 2007/0030443 A1 | 2/2007 | Chapoy et al. | |
| 2007/0093617 A1 | 4/2007 | DesNoyer et al. | |
| 2007/0105176 A1 | 5/2007 | Ibey | |
| 2007/0110672 A1 | 5/2007 | Bellott et al. | |
| 2007/0134290 A1 | 6/2007 | Rowland et al. | |
| 2007/0135698 A1 | 6/2007 | Shah et al. | |

(56) References Cited

U.S. PATENT DOCUMENTS

| | | |
|---|---|---|
| 2007/0244379 A1 | 10/2007 | Boock et al. |
| 2007/0270675 A1 | 11/2007 | Kane et al. |
| 2008/0020012 A1 | 1/2008 | Ju et al. |
| 2008/0075752 A1 | 3/2008 | Ratner et al. |
| 2008/0139903 A1 | 6/2008 | Bruce et al. |
| 2008/0249381 A1 | 10/2008 | Muller et al. |
| 2008/0311304 A1 | 12/2008 | Thompson et al. |
| 2009/0005663 A1 | 1/2009 | Parker et al. |
| 2009/0018425 A1 | 1/2009 | Ouyang et al. |
| 2009/0131773 A1 | 5/2009 | Struve et al. |
| 2009/0221891 A1 | 9/2009 | Yu et al. |
| 2009/0270953 A1 | 10/2009 | Ecker et al. |
| 2010/0113901 A1 | 5/2010 | Zhang et al. |
| 2010/0123121 A1 | 5/2010 | Taylor |
| 2010/0160749 A1 | 6/2010 | Gross et al. |
| 2010/0185066 A1 | 7/2010 | March |
| 2010/0249548 A1 | 9/2010 | Mueller |
| 2010/0303772 A1 | 12/2010 | McMillan et al. |
| 2011/0028806 A1 | 2/2011 | Merritt et al. |
| 2011/0036994 A1 | 2/2011 | Frayling |
| 2011/0224514 A1 | 9/2011 | Muller et al. |
| 2011/0230835 A1 | 9/2011 | Muller et al. |
| 2012/0123276 A1 | 5/2012 | Govari et al. |
| 2012/0140094 A1 | 6/2012 | Shpunt et al. |
| 2012/0165435 A1 | 6/2012 | Santhanam et al. |
| 2012/0172692 A1 | 7/2012 | Tamada et al. |
| 2012/0179014 A1 | 7/2012 | Shults et al. |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0215201 A1 | 8/2012 | Brauker et al. |
| 2012/0220979 A1 | 8/2012 | Brauker et al. |
| 2012/0226121 A1 | 9/2012 | Kamath et al. |
| 2012/0238852 A1 | 9/2012 | Brauker et al. |
| 2012/0245445 A1 | 9/2012 | Black et al. |
| 2012/0258551 A1 | 10/2012 | Herbrechtsmeier et al. |
| 2012/0265034 A1 | 10/2012 | Wisniewski et al. |
| 2012/0283538 A1 | 11/2012 | Rose et al. |
| 2012/0296311 A1 | 11/2012 | Brauker et al. |
| 2013/0004785 A1 | 1/2013 | Carlson et al. |
| 2013/0006069 A1 | 1/2013 | Gil et al. |
| 2013/0030273 A1 | 1/2013 | Tapsak et al. |
| 2013/0041200 A1 | 2/2013 | Sorokin et al. |
| 2013/0060105 A1 | 3/2013 | Shah et al. |
| 2013/0158413 A1* | 6/2013 | Lisogurski ......... A61B 5/14551 600/476 |
| 2013/0172699 A1 | 7/2013 | Rebec et al. |
| 2013/0211213 A1 | 8/2013 | Dehennis et al. |
| 2013/0213110 A1 | 8/2013 | Papadimitrakopoulos et al. |
| 2013/0213112 A1 | 8/2013 | Stumber |
| 2013/0229660 A1* | 9/2013 | Goldschmidt et al. ....... 356/445 |
| 2013/0231542 A1 | 9/2013 | Simpson et al. |
| 2013/0310666 A1 | 11/2013 | Shults et al. |
| 2013/0310670 A1 | 11/2013 | Boock et al. |
| 2013/0311103 A1 | 11/2013 | Cooper et al. |
| 2013/0313130 A1 | 11/2013 | Little et al. |
| 2013/0337468 A1 | 12/2013 | Muller et al. |
| 2014/0000338 A1 | 1/2014 | Luo et al. |
| 2014/0286875 A1 | 9/2014 | Gamsey et al. |
| 2014/0316224 A1 | 10/2014 | Sato |
| 2014/0357964 A1 | 12/2014 | Wisniewski et al. |
| 2014/0364707 A1 | 12/2014 | Kintz et al. |
| 2016/0213288 A1 | 7/2016 | Wisniewski et al. |
| 2016/0374556 A1 | 12/2016 | Colvin et al. |
| 2017/0087376 A1 | 3/2017 | McMillan et al. |
| 2017/0325722 A1 | 11/2017 | Wisniewski et al. |

FOREIGN PATENT DOCUMENTS

| | | |
|---|---|---|
| JP | 2004-537344 | 12/2004 |
| JP | 2007-044512 A | 2/2007 |
| JP | 2007-537805 A | 12/2007 |
| JP | 2009-540936 | 11/2009 |
| WO | WO 91/09312 | 6/1991 |
| WO | WO 97/19188 | 5/1997 |
| WO | WO 98/06406 | 2/1998 |
| WO | WO 98/22820 | 5/1998 |
| WO | WO 00/02048 | 1/2000 |
| WO | WO 01/18543 | 3/2001 |
| WO | WO 2001/075450 | 10/2001 |
| WO | WO 2002/087610 | 11/2002 |
| WO | WO 2003/006992 | 1/2003 |
| WO | WO 2005/120631 | 12/2005 |
| WO | WO 2006/004595 | 1/2006 |
| WO | WO 2006/010604 | 2/2006 |
| WO | WO 2006/044972 | 4/2006 |
| WO | WO 2006/065266 | 6/2006 |
| WO | WO 2006/130461 | 12/2006 |
| WO | WO 2007/126444 | 11/2007 |
| WO | WO 2008/105791 | 9/2008 |
| WO | WO 2008/141241 | 11/2008 |
| WO | WO 2008/142158 | 11/2008 |
| WO | WO 2008/143651 | 11/2008 |
| WO | WO 2009/106805 | 9/2009 |
| WO | WO 2010/037847 | 4/2010 |
| WO | WO 2010/133831 | 11/2010 |
| WO | WO 2010/141377 | 12/2010 |
| WO | WO 2011/101624 | 8/2011 |
| WO | WO 2011/101625 | 8/2011 |
| WO | WO 2011/101627 | 8/2011 |
| WO | WO 2011/101628 | 8/2011 |
| WO | WO 2012/027593 | 3/2012 |
| WO | WO 2012/048150 | 4/2012 |
| WO | WO 2013/073270 | 5/2013 |
| WO | WO 2013132400 A1 * | 9/2013 |
| WO | WO 2014/158988 | 10/2014 |
| WO | WO 2014/160258 | 10/2014 |
| WO | WO 2014/197786 | 12/2014 |

OTHER PUBLICATIONS

Examination Report for Australian Application No. 2011311889, dated Dec. 20, 2013.
Examination Report for Australian Application No. 2011311889, dated May 28, 2014.
Office Action for Chinese Application No. 201180057627.5, dated Dec. 15, 2014.
Notice of Reasons for Rejection for Japanese Application No. 2013-532954, dated Mar. 31, 2015.
International Search Report and Written Opinion for International Application No. PCT/US2011/055157, dated Jan. 23, 2012.
Office Action for U.S. Appl. No. 13/267,741, dated Mar. 20, 2015.
Office Action for U.S. Appl. No. 13/267,741, dated Apr. 1, 2014.
Office Action for U.S. Appl. No. 13/267,741, dated Oct. 7, 2015.
Office Action for U.S. Appl. No. 13/267,741, dated Nov. 20, 2014.
International Search Report and Written Opinion for International Application No. PCT/US2014/041284, dated Dec. 4, 2014.
Examination Report for Australian Application No. 2010256930, dated Dec. 18, 2013.
Examination Report for Australian Application No. 2010256930, dated Oct. 28, 2014.
Examination Report for Australian Application No. 2010256930, dated Feb. 13, 2015.
Office Action for Canadian Application No. 2,763,687, dated Aug. 5, 2015.
Office Action and Search Report for Chinese Application No. 201080033712.3, dated Jan. 5, 2013.
Office Action for Chinese Application No. 201080033712.3, dated Sep. 23, 2013.
Supplementary European Search Report for European Patent Application No. 10783874.0, dated Aug. 25, 2015.
Notice of Reasons for Rejection for Japanese Application No. 2012-514023, dated Mar. 18, 2014.
Decision of Final Rejection for Japanese Application No. 2012-514023, dated Jan. 6, 2015.
Office Action for U.S. Appl. No. 12/789,048, dated Sep. 29, 2014.
Office Action for U.S. Appl. No. 12/789,048, dated Nov. 25, 2014.
Office Action for U.S. Appl. No. 12/789,048, dated Dec. 5, 2012.
Office Action for U.S. Appl. No. 12/789,048, dated May 23, 2012.

(56) References Cited

OTHER PUBLICATIONS

International Search Report and Written Opinion for International Application No. PCT/US2010/036698, dated Feb. 9, 2011.
International Preliminary Report on Patenability in International Application No. PCT/US2010/036698, dated Dec. 6, 2011.
Office Action for U.S. Appl. No. 14/209,252, dated Apr. 14, 2015.
International Search Report and Written Opinion for International Application No. PCT/US2014/026183, dated Jul. 14, 2014.
International Preliminary Report on Patentability in International Application No. PCT/US2014/021298, dated Sep. 15, 2015.
Alexeev et al., "High ionic strength glucose-sensing protonic crystal," Anal. Chem., 75:2316-2323 (2003).
Alexeev et al., "Protonic crystal glucose-sensing material for non-invasive monitoring of glucose in tear fluid," Clinical Chemistry, 50(12):2353-2360 (2004).
Aslan et al., "Nanogold plasmon-resonance-based glucose sensing 2: wavelengthratiometric resonance light scattering," Anal. Chem., 77(7):2007-2014 (2005).
Badylak et al., "Immune response to biologic scaffold materials," Seminars in Immunology, 20(2):109-116 (2008).
Ballerstedt et al., "Competitive-binding assay method based on fluorescence quenching of ligands held in close proximity by a multivalent receptor," Anal. Chem., Acta. 345:203-212 (1997).
Bhardwaj, U. et al., "A review of the development of a vehicle for localized and controlled drug delivery for implantable biosensors," Journal of Diabetes Science and Technology, 2(6):1016-1029 (2008).
Billingsley et al., "Fluorescent nano-optodes for glucose detection, "Anal. Chem., 82(9):3707-3713 (2010).
Brasuel et al., "Fluorescent nanosensors for intracellular chemical analysis: decyl methacrylate liquid polymer matrix and ion-exchange-based potassium pebble sensors with real-time application to viable rat C6 glioma cells," Anal. Chem., 73(10):2221-2228 (2001).
Brasuel et al., "Liquid polymer nano-pebbles for CL-analysis and biological applications," Analyst, 128(10):1262-1267 (2003).
Braun et al., "Comparison of tumor and normal tissue oxygen tension measurements using oxylite or microelectrodes in rodents," Am. J. Physiol. Heart Circ. Physiol., 280(6):H2533-H2544 (2001).
Bridges et al., "Chronic inflammatory responses to microgel-based implant coatings," J Biomed. Mater. Res. A., 94(1):252-258 (2010).
Chaudhary et al., "Evaluation of glucose sensitive affinity binding assay entrapped in fluorescent dissolved-core alginate microspheres," Biotechnology and Bioengineering, 104(6):1075-1085 (2009).
Cordiero, P.G. et al., "The protective effect of L-arginine on ischemia-reperfusion injury in rat skin flaps," Plast Reconstruct Surg., 100(5):1227-1233 (1997).
Dunphy, I. et al., "Oxyphor R2 and G2: phosphors for measuring oxygen by oxygen-dependent quenching phosphorescence," Anal. Biochem., 310:191-198 (2002).
Garg, S. K. et al., "Improved glucose excursions using an implantable real-time continuous glucose sensor in adults with Type 1 diabetes," Diabetes Care, 27(3):734-738 (2004).
Henninger, N., et al., "Tissue response to subcutaneous implantation of glucose-oxidase-based glucose sensors in rats," Biosens Bioelectron, 23(1):26-34 (2007).
Horgan et al., "Crosslinking of phenylboronic acid receptors as a means of glucose selective holographic detection," Biosensors and Bioelectronics, 21(9):1838-1845 (2006).
Ibey et al., "Competitive binding assay for glucose based on glycodendrimer fluorophore conjugates," Anal. Chem., 77(21):7039-7046 (2005).
Isenhath et al., "A mouse model to evaluate the interface between skin and a percutaneous device," J Biomed. Mater. Research, 83A:915-922 (2007).
Ju, Y. M. et al., "A novel porous collagen scaffold around an implantable biosensor for improving biocompatibility. I. In vitrol in vivo stability of the scaffold and in vitro sensitivity of the glucose sensor with scaffold," J Biomed. Mater. Research, 87A:136-146 (2008), Available online Dec. 17, 2007.
Kaehr et al., "Multiphoton fabrication of chemically responsive protein hydrogels for microactuation," PNAS USA, 105(26):8850-8854 (2008).
Kasprzak, S. E., "Small-scale polymer structures enabled by thiol-ene copolymer systems," Doctoral Dissertation, Georgia Institute of Technology, May 2009.
Klimowicz, A. et al., "Evaluation of skin penetration of topically applied drugs by cutaneous microdialysis:acyclovir vs salicylic acid," J Clin Pharm Ther, 3(2):143-148 (2007).
Kloxin, A. M. et al., "Photodegradable hydrogels for dynamic tuning of physical and chemical properties," Science, 324:59-63 (2009).
Mansouri et al., "A minature optical glucose sensor based on affinity binding," Nature Biotechnology, 23:885-890 (1984).
Marshall et al., "Biomaterials with tightly controlled pore size that promote vascular in-growth," ACS Polymer Preprints, 45(2):100-101 (2004).
McShane et al., "Glucose monitoring using implanted fluorescent microspheres," IEEE Engineering in Medicine and Biology Magazine, 19(6):36-45 (2000).
Nagler, A. et al., "Topical treatment of cutaneous chronic graft versus host disease with halofuginone: a novel inhibitor of collagen Type 1 synthesis," Transplantation, 68(11):1806-1809 (1999).
Nielsen et al., "Clinical evaluation of a transcutaneous interrogated fluorescence lifetime-based microsensor for continuous glucose reading," J Diabetes and Technology, 3(1):98-109 (2009).
Nielson, R. et al., "Microreplication and design of biological architectures using dynamicmask multiphoton lithography," Small, 5(1):120-125 (2009).
Onuki, Y. et al., "A review of the biocompatibility of implantable devices: Current challenges to overcome foreign body response," Journal of Diabetes Science and Technology, 2(6):1003-1015 (2008).
Ostendorf, A. et al., "Two-photon polymerization: a new approach to micromachining," Photonics Spectra, 40(10):72-79 (2006).
Ozdemir et al., "Axial pattern composite prefabrication of high-density porous polyethylene: experimental and clinical research," Plast. Reconstr. Surg., 115(1):183-196 (2005).
Phelps et al., "Bioartificial matrices for therapeutic vascularization," PNAS USA, 107(8):3323-3328 (2010).
Pickup, J. C. et al., "In vivo glucose monitoring: the clinical reality and the promise," Biosens Bioelectron., 20(10)1897-1902 (2005), Available online Oct. 3, 2004.
Rounds et al., "Microporated peg spheres for fluorescent analyte detection," Journal of Fluorescence, 17(1):57-63 (2007), Available online Nov. 17, 2006.
Russell et al., "A fluorescence-based glucose biosensor using concanavalin A and dextran encapsulated in apoly(ethylene glycol) hydrogel," Anal. Chem., 71(15):3126-3132 (1999).
Sanders et al., "Tissue response to single polymer fibers of varying diameters: evaluation of fibrous encapsulation and macrophage density," J Biomed. Mater. Research, 52:231-237 (2000).
Sanders et al., "Tissue response to microfibers of different polymers: polyester, polyethylene, polylactic acid, and polyurethane," J Biomed. Mater. Research, 62(2):222-227 (2002).
Sanders et al., "Fibrous encapsulation of single polymer microfibers depends on their vertical dimension in subcutaneous tissue," J Biomed. Mater. Research, 67A:1181-1187 (2003).
Sanders et al., "Relative influence of polymer fiber diameter and surface charge on fibrous capsule thickness and vessel density for single-fiber implants," J Biomed. Mater. Research, 65A:462-467 (2003).
Sanders et al., "Polymer microfiber mechanical properties: a system for assessment and investigation of the link with fibrous capsule formation," J Biomed. Mater. Research, 67A:1412-1416 (2003).
Sanders et al., "Small fiber diameter fibro-porous meshes: tissue response sensitivity to fiber spacing," J Biomed Mater Research, 72A:335-342 (2005).
Sanders et al., "Fibro-porous meshes made from polyurethane micro-fibers: effects of surface charge on tissue response," Biomaterials, 26(7):813-818 (2005).

(56) References Cited

OTHER PUBLICATIONS

Schultz et al., "Affinity sensor: a new technique for developing implantable sensors for glucose and other metabolites," Diabetes Care, 5(3)245-253 (1982).
Smith, J. L., "The Pursuit of Noninvasive Glucose: 'Hunting the Deceitful Turkey,'" (2006).
Srivastava et al., "Application of self-assembled ultrathin film coatings to stabilize macromolecule encapsulation in alginate microspheres," J of Microencapsulation, 22(4):397-411 (2005).
Srivasta et al., "Stabilization of glucose oxidase in alginate microspheres with photo reactive diazoresin nanofilm coatings," Biotechnology and Bioengineering, 91(1):124-131 (2005).
Takano et al., "An oxo-bacteriochlorin derivative for long-wavelength fluorescence ratiometric alcohol sensing," Analyst, 135:2334-2339 (2010).
Tian et al., "Dually fluorescent sensing of PH and dissolved oxygen using a membrane made from polymerizable sensing monomers," Sensors and Actuators B, 147:714-722 (2010).
Tian et al., "Influence of matrices on oxygen sensing of three-sensing films with chemically conjugated platinum porphyrin probes and preliminary application for monitoring of oxygen consumption of *Escherichia coli* (*E. coli*)," Sensors and Actuators B, 150:579-587 (2010).
Tian, Y. et al., "A New Cross-linkable Oxygen Sensor Covalently Bonded into Poly(2-hydroxyethyl methacrylate)-co-Polyacrylamide Thin Film for Dissolved Oxygen Sensing," Chem. Mater, 22:2069-2078 (2010).
Vidavalur, R. et al., "Sildenafil induces angiogenic response in human coronary arterioloar endothelial cells through the expression of thioredoxin, hemaoxygenase, and VEGF," Vasc Pharm, 45(2):91-95 (2006).
Ward, W. K. et.al., "The effect of microgeometry, implant thickness and polyurethane chemistry on the foreign body response to subcutaneous implants," Biomaterials, 23(21):4185-4192 (2002).
Wisniewski, N. et.al., "Characterization of implantable biosensor membrane fouling," Fresen J Anal Chem., 366 (6-7):611-621 (2000).
Wisniewski, N. et. al., "Methods for reducing biosensor membrane biofouling," Colloids and Surfaces B: Biointerfaces, 18:197-219 (2000).
Woderer, S., "Continuous glucose monitoring in interstitial fluid using glucose oxidase-based sensor compared to established blood glucose measurement in rats," Anal Chim Acta., 581(1):7-12 (2007), Epub Aug. 18, 2006.
Office Action for U.S. Appl. No. 12/789,048, dated Dec. 14, 2015.
Notice of Reasons for Rejection for Japanese Application No. 2016-500748, dated Feb. 26, 2018, 8 pages.
Examination Report No. 1 for Australian Application No. 2014241420, dated Sep. 1, 2017, 3 pages.
First Office Action for Chinese Application No. 201480016308.3, dated Mar. 29, 2017, 16 pages.
Supplementary European Search Report for European Application No. 14775668.8, dated Oct. 13, 2016.
Shibata, H. et al., "Injectable hydrogel microbeads for fluorescence-based in vivo continuous glucose monitoring", Proceedings of the National Academy of Sciences of the United States of America, Oct. 19, 2010, vol. 107, No. 42, pp. 17894-17898.
Young et al., "A novel porous collagen scaffold around an implantable biosensor for improving biocompatibility. I. In vitro/in vivo stability of the scaffold and in vitro sensitivity of the glucose sensor with scaffold," Journal of Biomedical Materials Research Part A., 2008, vol. 87, pp. 136-146.

* cited by examiner

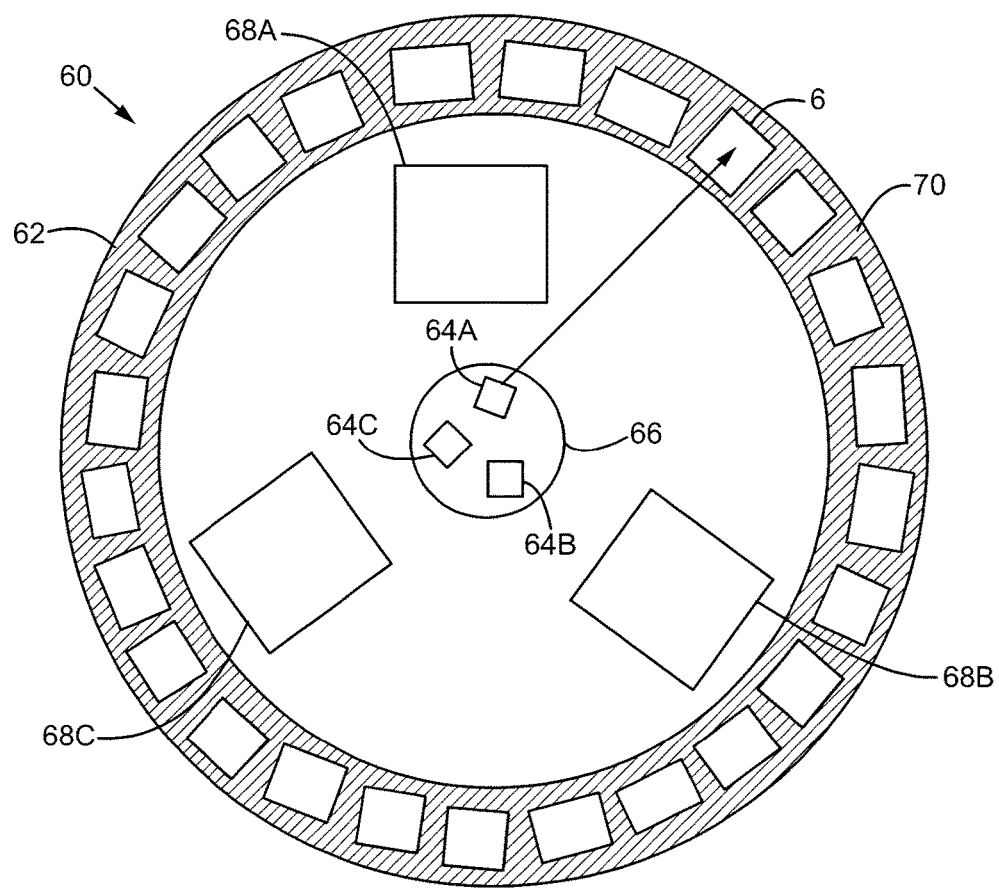
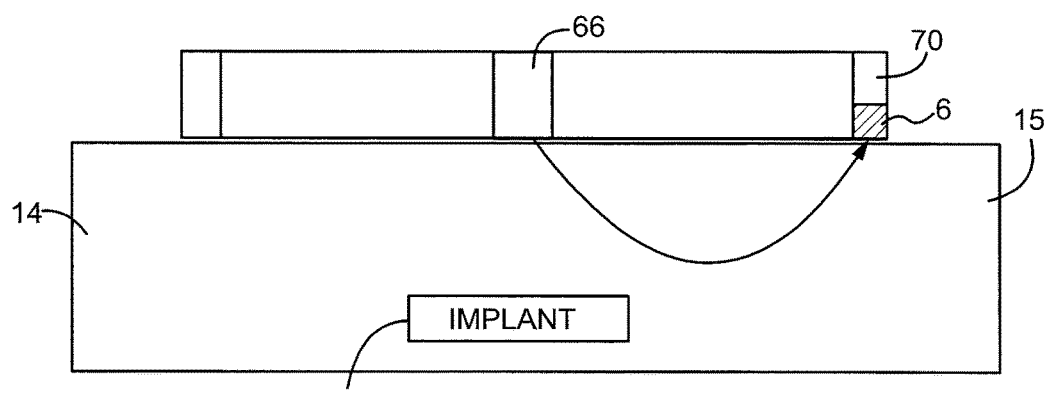

METHOD AND DEVICE FOR CORRECTING OPTICAL SIGNALS

CROSS REFERENCE TO RELATED APPLICATIONS

This application claims the benefit of U.S. provisional patent application 61/785,087 filed on Mar. 14, 2013, titled "Method and Device for Correcting Optical Signals", which application is hereby incorporated by reference in its entirety.

BACKGROUND

The invention relates to a method and device for monitoring an implant, and in particular to a method and device for correcting luminescent signals emitted from the implant.

The monitoring of the level of analyte, such as glucose, lactate or oxygen, in certain individuals is important to their health. High or low levels of glucose, or other analytes, may have detrimental effects or be indicative of specific health states. The monitoring of glucose is particularly important to individuals with diabetes, a subset of whom must determine when insulin is needed to reduce glucose levels in their bodies or when additional glucose is needed to raise the level of glucose in their bodies.

A conventional technique used by many individuals with diabetes for personally monitoring their blood glucose level includes the periodic drawing of blood, the application of that blood to a test strip, and the determination of the blood glucose level using calorimetric, electrochemical, or photometric detection. This technique does not permit continuous or automatic monitoring of glucose levels in the body, but typically must be performed manually on a periodic basis. Unfortunately, the consistency with which the level of glucose is checked varies widely among individuals. Many people with diabetes find the periodic testing inconvenient, and they sometimes forget to test their glucose level or do not have time for a proper test. In addition, some individuals wish to avoid the pain associated with the test. Unmonitored glucose may result in hyperglycemic or hypoglycemic episodes. An implanted sensor that monitors the individual's analyte levels would enable individuals to monitor their glucose, or other analyte levels, more easily.

A variety of devices have been developed for monitoring of analytes (e.g., glucose) in the blood stream or interstitial fluid of various tissues. A number of these devices use sensors that are inserted into a blood vessel or under the skin of a patient. These implanted sensors are often difficult to read or to monitor optically, because of low levels of florescence in the presence of high scatter due to dynamic changes in skin conditions (e.g., blood level and hydration). The skin is highly scattering, and the scattering may dominate the optical propagation. Scatter is caused by index of refraction changes in the tissue, and the main components of scatter in the skin are due to lipids, collagen, and other biological components. The main absorption is caused by blood, melanin, water, and other components.

One device, disclosed in published US patent application 20090221891 to Yu, includes components of an assay for glucose. An optical signal is read out transcutaneously by external optics when the sensor is implanted in vivo. A fluorimeter separately measures, for a donor chromophore and an acceptor chromophore, an excitation light intensity, an ambient light intensity, and an intensity of combined luminescent and ambient light. Measurements are taken by holding the fluorimeter close to the skin and in alignment with the sensor. The final output provided is the normalized ratio between the luminescent intensity from the two fluorophores, which may be converted to analyte concentration using calibration data. A calibration curve is established empirically by measuring response versus glucose concentration. Although this device provides some light signal correction, it may still be difficult to obtain accurate readings due to dynamic skin changes that cause optical scattering and absorption of light emitted from the implant.

US patent application 20110028806 to Merritt discloses another procedure and system for measuring blood glucose levels. A set of photodiodes detects the luminescence and reflectance of light energy emitted from one or more emitters, such as LEDs, into a patient's skin. Small molecule metabolite reporters (SMMRs) that bind to glucose are introduced to tissue of the stratum corneum and the epidermis to provide more easily detected luminescence. The test results are calibrated with a reflectance intensity measurement taken at approximately the excitation wavelength. In addition, the method includes measuring a second luminescence and reflectance intensity to normalize data from the first set of measurements. First luminescence and reflectance intensity measurements are taken at a site treated with an SMMR. Second luminescence and reflectance intensity measurements are taken at an untreated, background site. The background measurement is then used to correct for the background tissue luminescence and absorption through a wavelength normalization. Although this method provides some light signal correction for background luminescence and reflectance, it may still be difficult to obtain accurate and/or consistent glucose readings from glucose-binding molecules in the epidermis.

There is still a need for a small, compact device that can accurately and consistently monitor an implanted sensor and provide signals to an analyzer without substantially restricting the movements and activities of a patient. Continuous and/or automatic monitoring of the analyte can provide a warning to the patient when the level of the analyte is at or near a threshold level. For example, if glucose is the analyte, then the monitoring device might be configured to warn the patient of current or impending hyperglycemia or hypoglycemia. The patient can then take appropriate actions.

SUMMARY

According to one aspect, a method is provided for correcting at least one analyte-dependent optical signal emitted from an implant. The implant is typically embedded in tissue of a mammalian body. The implant is capable of emitting, in response to excitation light within an excitation wavelength range, the analyte-dependent optical signal within an emission wavelength range. The method comprises transmitting first excitation light within the excitation wavelength range through the tissue to the implant and measuring a first optical signal emitted from the tissue, within the emission wavelength range, in response to the first excitation light. The method also comprises transmitting second excitation light within the emission wavelength range into the tissue and measuring a second optical signal emitted from the tissue, within the emission wavelength range, in response to the second excitation light. At least one corrected signal value is calculated in dependence upon the measured signals.

According to another aspect, an optical detection device is provided for monitoring an implant embedded in tissue of a mammalian body. The implant is capable of emitting, in response to excitation light within an excitation wavelength range, at least one analyte-dependent optical signal within an emission wavelength range. The device comprises a first light source arranged to transmit first excitation light within the excitation wavelength range through the tissue to the implant. A second light source is arranged to transmit second excitation light within the emission wavelength range into the tissue. At least one detector is arranged to measure, in response to the first excitation light, a first optical signal emitted from the tissue in the emission wavelength range and arranged to measure, in response to the second excitation light, a second optical signal emitted from the tissue in the emission wavelength range.

According to another aspect, a method is provided for correcting at least one analyte-dependent optical signal emitted from an implant embedded in tissue of a mammalian body. The implant is capable of emitting, in response to excitation light within an excitation wavelength range, the analyte-dependent optical signal within an emission wavelength range. The method comprises transmitting first excitation light within the excitation wavelength range through the tissue to the implant and measuring a first optical signal emitted from the tissue, within the emission wavelength range, in response to the first excitation light. The method also comprises transmitting second excitation light within the excitation wavelength range into the tissue and measuring a second optical signal emitted from the tissue, within the emission wavelength range, in response to the second excitation light. The second excitation light and the light emitted in response to the second excitation light form a light path that is spaced laterally from the implant a sufficient distance to avoid significant contribution from implant reporters (e.g., luminescent, luminescent, bioluminescent, or phosphorescent reporters). At least one corrected signal value is calculated in dependence upon the measured optical signals.

According to another aspect, an optical detection device is provided for monitoring an implant embedded in tissue of a mammalian body. The implant is capable of emitting, in response to excitation light within an excitation wavelength range, at least one analyte-dependent optical signal within an emission wavelength range. The device comprises a first light source arranged to transmit first excitation light in the excitation wavelength range through the tissue to the implant. A first detector is arranged to measure, in response to the first excitation light, a first optical signal emitted from the tissue in the emission wavelength range. A second light source is arranged to transmit second excitation light within the excitation wavelength range into the tissue. A second detector is arranged to measure, in response to the second excitation light, a second optical emitted from the tissue in the emission wavelength range. The second light source and the second detector are positioned with respect to each other such that the second excitation light and the light emitted in response to the second excitation light form a light path that is spaced laterally from the implant a sufficient distance to avoid significant contribution from implant reporters.

BRIEF DESCRIPTION OF THE DRAWINGS

The foregoing aspects and advantages of the present invention will become better understood upon reading the following detailed description and upon reference to the drawings where:

FIG. 4 shows a schematic plan view of an optical detection device according to another embodiment of the invention.

FIG. 5 shows a schematic cross-sectional view of the device of FIG. 4.

DETAILED DESCRIPTION OF PREFERRED EMBODIMENTS

In the following description, it is understood that all recited connections between structures can be direct operative connections or indirect operative connections through intermediary structures. A set of elements includes one or more elements. Any recitation of an element is understood to refer to at least one element. A plurality of elements includes at least two elements. Unless otherwise required, any described method steps need not be necessarily performed in a particular illustrated order. A first element (e.g. data) derived from a second element encompasses a first element equal to the second element, as well as a first element generated by processing the second element and optionally other data. Making a determination or decision according to a parameter encompasses making the determination or decision according to the parameter and optionally according to other data. Unless otherwise specified, an indicator of some quantity/data may be the quantity/data itself, or an indicator different from the quantity/data itself. Computer programs described in some embodiments of the present invention may be stand-alone software entities or sub-entities (e.g., subroutines, code objects) of other computer programs. Computer readable media encompass non-transitory media such as magnetic, optic, and semiconductor storage media (e.g. hard drives, optical disks, flash memory, DRAM), as well as communications links such as conductive cables and fiber optic links According to some embodiments, the present invention provides, inter alia, computer systems comprising hardware (e.g. one or more processors and associated memory) programmed to perform the methods described herein, as well as computer-readable media encoding instructions to perform the methods described herein.

The following description illustrates embodiments of the invention by way of example and not necessarily by way of limitation.

Figure 1:
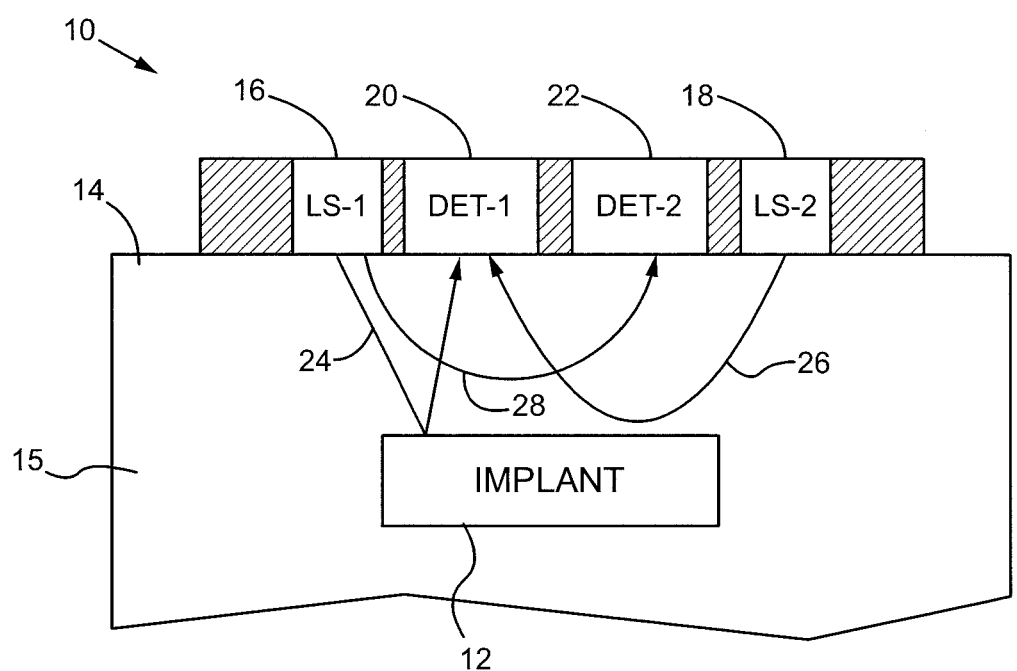
FIG. 1 shows a schematic side view of an optical detection device for monitoring an implant according to one embodiment of the invention.

FIG. 1 shows a schematic side view of an optical detection device 10 for monitoring an implanted sensor or implant 12, according to a first embodiment of the invention. The implant 12 is embedded in tissue of a mammalian body (which may be a portion of tissue that is attached or unattached to the rest of the body in various embodiments). The implant 12 is typically embedded under a surface of skin 14. The implant 12 is embedded at a first depth under the surface of the skin 14, which is preferably a sufficient depth to position the implant in the subcutaneous tissue (e.g., in the range of 1 to 5 mm under the surface of the skin 14). In some embodiments, the implant 12 is embedded in the tissue at a depth greater than or equal to 2 mm under the surface of the skin 14, and in other embodiments the implant 12 is embedded in the tissue at a depth greater than or equal to 4 mm under the surface of the skin.

The implant 12 is capable of emitting, in response to excitation light within an excitation wavelength range, at least one analyte-dependent optical signal within an emission wavelength range. The analyte may comprise, for example, glucose or other analytes in the body of the individual. Suitable optical signals include, but are not limited, to luminescent, luminescent, bioluminescent, phosphorescent, autoluminescence, and diffuse reflectance signals. In preferred embodiments, the implant 12 contains one or more luminescent dyes whose luminescence emission intensity varies in dependence upon the amount or presence of target analyte in the body of the individual.

A first light source 16 is arranged to transmit first excitation light within the excitation wavelength range from the surface of the skin 14 to the implant 12. A second light source 18 is arranged to transmit second excitation light from the surface of the skin 14 into the tissue 15. The second excitation light is preferably within the emission wavelength range of the analyte-dependent luminescent signal (e.g., the emission peak). Suitable light sources include, without limitation, lasers, semi-conductor lasers, light emitting diodes (LEDs), organic LEDs.

At least one detector, and more preferably at least two detectors 20, 22 are arranged with the light sources 16, 18. The first detector 20 is positioned to measure, in response to the first excitation light from the first light source 16, a first optical signal (e.g., the intensity of light) emitted at the surface of the skin 14 within the emission wavelength range. The detector 20 is also arranged to measure, in response to the second excitation light, a second optical signal emitted from the tissue 15 through the surface of the skin 14 within the emission wavelength range. Suitable detectors include, without limitation, photodiodes or CCDs. Although multiple detectors are preferred for some embodiments, one could use a single universal detector. The detectors 20, 22 are preferably filtered (e.g., dichroic filters or other suitable filters) to measure the optical signals emitted within respective wavelength ranges. In this example, a suitable luminescent dye sensitive to glucose concentration is Alexa 647 responsive to excitation light (absorption) in the range of about 600 to 650 nm (absorption peak 647 nm) and within an emission wavelength range of about 670 to 750 nm with an emission peak of about 680 nm.

In the operation of device 10, an analyte-dependent luminescent signal emitted from the implant 12 is corrected for diffuse reflectance and/or autofluorescence. The light source 16 is activated to transmit first excitation light within the excitation wavelength range from the surface of the skin 14 to the implant 12. The first detector 20 measures, in response to the first excitation light, a first optical signal emitted from the tissue 15 at the surface of the skin 14 within the emission wavelength range, as represented by a first light path 24 from the light source 16 to the implant 12 to the first detector 20. The light path 24 provides the primary analyte-dependent optical signal. The second light source 18 is activated to transmit second excitation light from the surface of the skin 14 to a second depth in the tissue 15 under the surface of the skin 14. The second excitation light is substantially within the emission wavelength range (e.g., the emission peak) of the analyte-dependent luminescent signal. The first detector 20 measures, in response to the second excitation light, a second optical signal emitted from the tissue 15 through the surface of the skin 14 within the emission wavelength range, as represented by a second light path 26.

The second optical signal may be used as a reference signal to correct the primary analyte-dependent optical signal for diffuse reflectance or scattering of light in the tissue 15. In some embodiments, the second depth to which the light path 26 extends below the surface of the skin 14 may be substantially equal to the first depth at which the implant 12 is embedded (e.g., in the subcutaneous tissue at a depth of 1 to 5 mm under the surface of the skin 14). In some embodiments, the light path 26 for the second optical signal extends to a depth greater than or equal to 2 mm under the surface of the skin 14, and in other embodiments the light path 26 for the second optical signal extends to a depth greater than or equal to 4 mm under the surface of the skin.

An additional correction factor may optionally be obtained by activating the first light source 16 to transmit third excitation light, within the excitation wavelength range, from the surface of the skin 14 to a third depth in the tissue 15. In some embodiments, the third depth may differ from the first and second depths, and the third depth may be in the range of 1 to 5 mm under the surface of the skin 14. The second detector 22 measures a third optical signal emitted from the tissue 15 through the surface of the skin 14 within the excitation wavelength range in response to the third excitation light, as represented by a third light path 28. At least one corrected signal value is calculated in dependence upon the measured optical signals. In one example, the primary analyte-dependent signal from the implant may be corrected as:

$$\text{Corrected Signal} = S(LS1, D1) * C(LS2, D1) * C(LS1, D2) \qquad (1)$$

In equation (1) above, the term S(LS1, D1) represents the first optical signal, which is the primary analyte-dependent optical signal measured from the first light path 24 from the first light source 16 to the implant 12 to the first detector 20. The term C(LS2, D1) represents the second optical signal, which is a correction factor signal measured from the second light path 26 from the second light source 18 to the first detector 20. The term C(LS1, D2) represents an optional third optical signal, which is an additional correction factor signal measured from the third light path 28 from the first light source 16 to the second detector 22.

Thus, the primary analyte-dependent optical signal emitted from the implant 12 may be corrected for diffuse reflectance or scattering within the emission wavelength range of the analyte-dependent optical signal, to account for optical scattering or absorption of the signal in the tissue 15. The analyte-dependent optical signal may optionally be corrected for scattering, reflectance or attenuation in the excitation wavelength range to account for dynamic changes in skin properties. One advantage of correcting the analyte-dependent signal by one or more reference signals is that accurate and/or consistent glucose values may be determined from measurements of light emitted from an implant located relatively deep in the tissue, such as in the subcutaneous region. Light emitted from the implant 12 may be strongly modulated by the tissue 15 between the implant and the surface of the skin 14. Embodiments of the present invention provide means to correct for modulation of light emitted from the tissue 15, in addition to correction for excitation light and background or ambient light, if desired.

Another advantage is that measurements of the reference optical signals used for correction factors (such as diffuse reflectance, autofluorescence, and/or background light) are taken in the same region of tissue 15 in which the implant 12 is embedded in a few seconds of time or less, so that dynamic skin or tissue properties, that may vary within different regions of the body, are substantially the same for the correction signals as they are for the primary analyte-dependent signal at the time of measurement. Prior to executing optical reads for the analyte-dependent signal, the diffuse reflectance correction signal and/or the autofluorescence correction signal, a dark reading may be taken to account for background or ambient light, and this reading may be used to further correct the signals, e.g., by background subtraction. A preferred order of optical readings for the correction factors is background subtraction, autofluorescence correction, and diffuse reflectance correction, although no particular order is required.

In some embodiments, an analyte concentration (e.g., glucose level) is determined from the corrected signal value. Preferably a look-up table or calibration curve is used to determine the analyte concentration in dependence upon the corrected signal value. The look-up table or calibration curve may be in a microprocessor included with the optics. In some embodiments, the microprocessor is programmed to store measured signal values and/or to calculate corrected signal values. Alternatively, these functions may be performed in a separate processor or external computer in communication with the optical device. The external processor or computer receives data representative of the measured optical signals and calculates the corrected signal value and analyte concentration. Alternatively, multiple processors may be provided, e.g., providing one or more processors in the optical device that communicate (wirelessly or with wires) with one or more external processors or computers.

Figure 2:
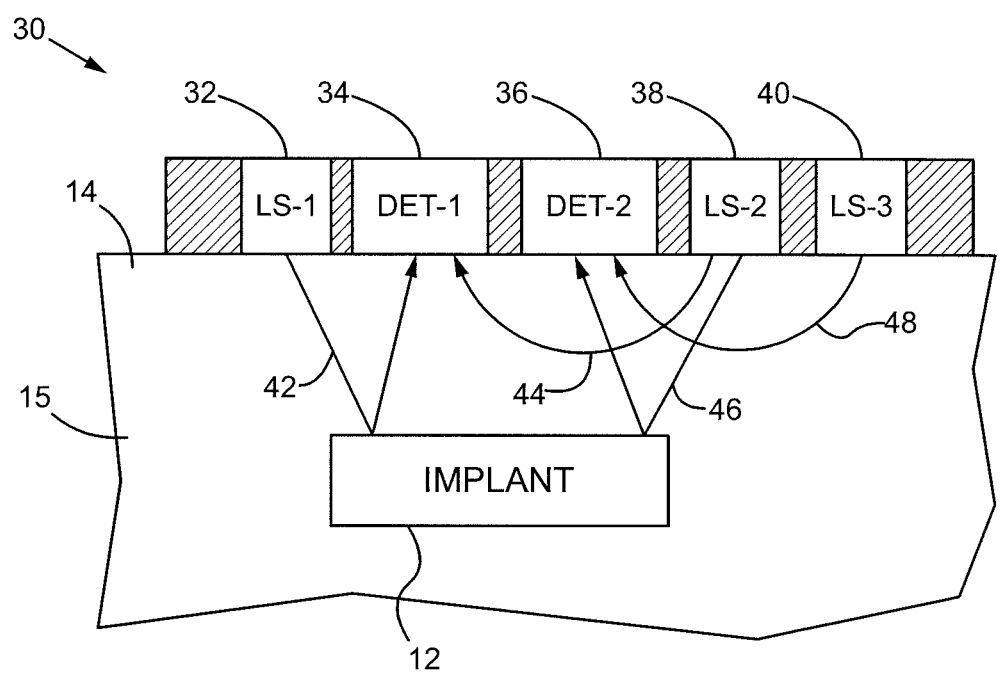
FIG. 2 shows a schematic side view of an optical detection device for monitoring an implant according to another embodiment of the invention.

FIG. 2 shows another embodiment of an optical detection device 30 for monitoring an implant 12. In this embodiment, the implant 12 is further capable of emitting, in response to excitation light within a second excitation wavelength range (that may share or overlap the first emission wavelength range) at least one analyte-independent optical signal within a second emission wavelength range. The implant 12 preferably contains an analyte-independent luminescence dye that functions to control for non-analyte physical or chemical effects on a reporter dye (e.g., photo bleaching or pH). Multiple dyes may used. The analyte-independent optical signal is not modulated by analyte present in the tissue 15 and provides data for normalization, offset corrections, or internal calibration. The analyte-independent signal may compensate for non-analyte affects that are chemical or physiological (e.g., oxygen, pH, redox conditions) or optical (e.g., water, light absorbing/scattering compounds, hemoglobin). Alternatively, the analyte-independent signal may be provided by a stable reference dye in the implant 12. Suitable stable reference materials include, but are not limited to, lanthanide doped crystals, lanthanide doped nanoparticles, quantum dots, chelated lanthanide dyes, and metal (e.g., gold or silver) nanoparticles. The stable reference dye may provide a reference signal for other signals (e.g., to determine photo bleaching).

The second embodiment differs from the first embodiment described above in that the device 30 includes a third light source 40 for transmitting excitation light into the tissue 15 through the surface of the skin 14. In the operation of device 30, an analyte-dependent luminescent signal emitted from the implant 12 is corrected using three reference signals. The first light source 32 is activated to transmit excitation light within a first excitation wavelength range from the surface of the skin 14, through the tissue 15, to the implant 12. The first detector 34 measures, in response to the first excitation light, a first optical signal emitted from the tissue 15 at the surface of the skin 14 within a first emission wavelength range, as represented by a first light path 42 from the first light source 32, to the implant 12, and to the first detector 34. This first optical signal is the primary analyte-dependent optical signal.

The second light source 38 is activated to transmit second excitation light from the surface of the skin 14 to a second depth in the tissue 15. The second excitation light is preferably within the first emission wavelength range (e.g., the emission peak) of the primary analyte-dependent optical signal. The first detector 34 measures, in response to the second excitation light, a second optical signal emitted from the tissue 15 at the surface of the skin 14 within the emission wavelength range, as represented by a second light path 44. The second optical signal may be used to correct for diffuse reflectance or scattering of light in the tissue 15 between the implant 12 and the surface of the skin 14. In some embodiments, the depth of the second light path 44 may be substantially equal to the first depth at which the implant 12 is embedded (preferably in the subcutaneous tissue 1 to 5 mm under the surface of the skin 14). In some embodiments, the light path 44 for the second optical signal extends to a depth greater than or equal to 2 mm under the surface of the skin 14, and in other embodiments the light path 44 for the second optical signal extends to a depth greater than or equal to 4 mm under the surface of the skin.

Next, the light source 38 is activated to transmit third excitation light in the second excitation wavelength range from the surface of the skin 14 to the implant 12. The second detector 36 measures, in response to the third excitation light, a third optical signal emitted from the tissue 15 at the surface of the skin 14 within the second emission wavelength range, as represented by a third light path 46. In this embodiment, the third optical signal is the analyte-independent luminescent signal. Next, the third light source 40 is activated to transmit fourth excitation light from the surface of the skin 14 into the tissue 15. The fourth excitation light is preferably within the emission wavelength range of the analyte-independent luminescent signal. The detector 36 measures, in response to the fourth excitation light, a fourth optical signal emitted from the tissue 15 at the surface of the skin 14 within this emission wavelength range, as represented by a fourth light path 48. At least one corrected signal value is calculated in dependence upon the measured optical signals. In one example, the primary analyte-dependent signal from the implant 12 may be corrected as:

$$\text{Corrected Signal} = S(LS1,D1)*C(LS2,D1)/[S(LS2,D2)*C(LS3,D2)] \tag{2}$$

In equation (2) above, the term $S(LS1, D1)$ represents the first optical signal which is the primary analyte-dependent signal measured from the first light path 42 from the first light source 32 to the implant 12 to the first detector 34. The term C(LS2, D1) represents the second optical signal, which is a correction factor signal measured from the second light path 44 from the second light source 38 to the first detector 34. The term S(LS2, D2) represents the third optical signal, which is the analyte-independent signal measured from the third light path 46 extending from the second light source 38 to the implant 12 to the second detector 36. The term C(LS3, D2) represents the fourth optical signal, which is a correction factor signal measured from the fourth light path 48 extending from the third light source 40 to the second detector 36.

In some embodiments in which two implant reporters (e.g., luminescent dyes) are utilized, it is possible that the implant reporters may share or overlap excitation (absorption) or emission wavelength ranges. For example, in the embodiment of FIG. 2, the emission wavelength range of the first dye, which provides the analyte-dependent luminescence signal, shares or overlaps the excitation wavelength range of the second dye, which provides the analyte-independent luminescence signal. In another embodiment, the first and second dyes may share or overlap excitation wavelength ranges (so that a common light source may be used) and emit optical signals within different emission wavelength ranges. In another embodiment, the first and second dyes may be excited by light within different excitation wavelength ranges and emit optical signals within the same or overlapping emission wavelength range(s).

Figure 3:
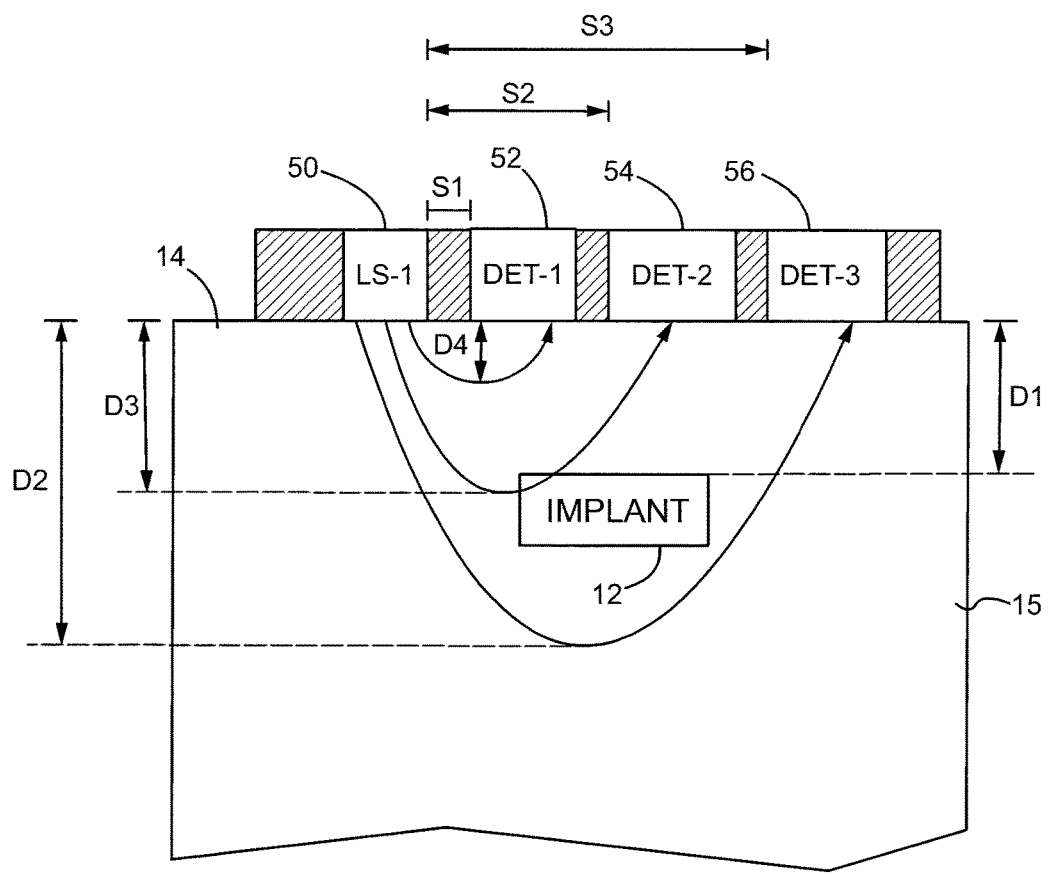
FIG. 3 shows a schematic side view of aspects of an optical detection device according to another embodiment of the invention.

FIG. 3 shows optical interrogation at different depths D2, D3, D4 in the tissue 15 relative to the first depth D1 of the implant 12 under the surface of the skin 14. The spacing distances S1, S2, S3 between the arrangement of detectors 52; 54, 56 and the light source 50 determines the depths D2, D3, D4 of the respective light paths. In some embodiments, readings for optical signal corrections are performed at multiple depths, as represented by the respective light paths, and the measured values of the reference optical signals used for correction are averaged for the correction factor. In some embodiments, the light path for the reference optical signal extends to a depth D2 in the tissue 15 that is greater than the depth D1 at which the implant 12 is embedded. The light path for the reference optical signal may also extend to a depth D3 in the tissue 15 such that the light path passes through the implant 12.

When the optical device has multiple possible combinations of spacing distances between the light sources and detectors as shown in FIGS. 3-9, implementation may be more flexible, because the depth of the implant 12 may be application-specific. In one embodiment, at least one analyte-independent signal, which may be emitted by the stable reference dye, is used to determine the appropriate depth for the light path(s) and resulting optical signal(s) measured to correct the analyte-dependent signal for diffuse reflectance and/or autofluorescence. Preferably a look-up table is used to determine, based on the measured intensity of the analyte-independent luminescent signal emitted from the implant, which of the possible depth(s) for normalization optical signals should be used, or more specifically which light source/detector pairing(s). The look-up table may be in a microprocessor included with the optical device, or in a separate processor or external computer in communication with the optical device that receives data representative of the measured optical signals (e.g., intensities of light measured within selected wavelengths).

In some embodiments, the processor is programmed to determine (e.g., by calculation or a look-up table) a quantity or weight assigned to measurements of one or more diffuse reflectance signals. The quantity or weight assigned to the measured diffuse reflectance signal may then be used in correcting or normalizing one or more implant reporter signals (e.g., the primary analyte-dependent signal emitted from the implant) to calculate the corrected signal value. The quantity or weight is preferably determined in dependence upon the intensity of an analyte-independent optical signal (e.g., from the stable reference dye). The intensity of the analyte-independent optical signal may vary with the depth of the implant in the tissue. For example, if the implant is embedded in tissue at a depth of 2 mm under the surface of the skin, the amount of light attenuation in the tissue will likely be less than if the implant were embedded at a depth of 4 mm. Reporter optical signals emitted from a shallower implant may require less of a correction factor for diffuse reflectance and/or autofluorescence than those signals emitted from an implant embedded at a greater depth. In some embodiments, the diffuse reflectance correction factor used to correct or normalize the analyte-dependent signal is proportional to depth, and the quantity or weight assigned to the diffuse reflectance measurement is determined in dependence upon the measurement of the analyte-independent signal.

FIG. 4 shows another embodiment of an optical device 60 having additional light sources and detectors with multiple possible combinations of spacing distances between the light sources and detectors. The light sources and detectors are arranged in a sensor patch 62 adapted to be placed on the surface of the skin, and described in greater detail below. At least one, and more preferably three central exciter light sources 64A, 64B, and 64C are positioned to transmit excitation light through a central via 66 in the patch 62. The central via 66 may contain one or more optical waveguide (s). At least one detector, and more preferably an inner ring of three central detectors 68A, 68B, and 68C are arranged around the central via 66. There is also preferably an outer ring 70 having multiple outer-ring exciter light sources and outer-ring detectors (in this example twenty-five outer-ring light sources and detectors) arranged in a substantially ring-shaped pattern, providing many permutations of possible optical channels. The combination of an excitation light source and a detection band is an optical channel. An example of one possible implementation of the optical device 60 will now be given with reference to FIGS. 4-11 and Table 1, describing twelve optical channels.

TABLE 1

| Optical Channel | Function | Excitation | Emissions Detected | Exciter | Detector | Comments |
|---|---|---|---|---|---|---|
| 1 | Implant Reporter 1 | Excitation Peak Reporter 1 | Emission Peak Reporter 1 | Central Exciter 1 | Central Detector 1 | Analyte-dependent 1 |
| 2 | Implant Reporter 2 | Excitation Peak Reporter 2 | Emission Peak Reporter 2 | Central Exciter 2 | Central Detector 2 | Analyte-independent 1 |
| 3 | Implant Reporter 3 | Excitation Peak Reporter 3 | Emission Peak Reporter 3 | Central Exciter 3 | Central Detector 3 | Stable Reference dye |

TABLE 1-continued

| Optical Channel | Function | Excitation | Emissions Detected | Exciter | Detector | Comments |
|---|---|---|---|---|---|---|
| 4 | Exciter Power Normalization | Excitation Peak Reporter 1 | Excitation Peak Reporter 1 | Central Exciter 1 | Outer Detector 6 | Power Normalization 1 |
| 5 | Exciter Power Normalization | Excitation Peak Reporter 2 | Excitation Peak Reporter 2 | Central Exciter 2 | Outer Detector 6 | Power Normalization 2 |
| 6 | Exciter Power Normalization | Excitation Peak Reporter 3 | Excitation Peak Reporter 3 | Central Exciter 3 | Outer Detector 6 | Power Normalization 3 |
| 7 | Diffuse Reflectance 1 | Emission Peak Reporter 1 | Emission Peak Reporter 1 | Outer Exciter 6 | Outer Detector 6 | Diffuse Reflectance Data |
| 8 | Diffuse Reflectance 2 | Emission Peak Reporter 2 | Emission Peak Reporter 1 | Outer Exciter 7 | Outer Detector 6 | Diffuse Reflectance Data |
| 9 | Diffuse Reflectance 3 | Emission Peak Reporter 3 | Emission Peak Reporter 1 | Outer Exciter 8 | Outer Detector 6 | Diffuse Reflectance Data |
| 10 | Autofluorescence 1 | Excitation Peak Reporter 1 | Emission Peak Reporter 1 | Outer Exciter 1 | Outer Detector 1 | Autofluorescence and ambient light |
| 11 | Autofluorescence 2 | Excitation Peak Reporter 2 | Emission Peak Reporter 2 | Outer Exciter 2 | Outer Detector 2 | Autofluorescence and ambient light |
| 12 | Autofluorescence 3 | Excitation Peak Reporter 3 | Emission Peak Reporter 3 | Outer Exciter 3 | Outer Detector 3 | Autofluorescence and ambient light |

As shown in Table 1, optical channels 1-3 function to measure three reporter dye signals from the implant, including an analyte-specific signal, an analyte-independent signal, and a stable reference dye signal. Optical channel 1 functions to measure an analyte-specific luminescent signal from the implant, such as a light signal whose intensity varies with glucose level. Other embodiments may include multiple analyte-dependent signals from the implant. Optical channel 2 functions to measure an analyte-independent control for non-analyte physical or chemical effects on the reporter dyes (e.g., photo bleaching, pH). Optical channel 3 functions to measure a stable reference dye (e.g., lanthanide).

Figure 6:
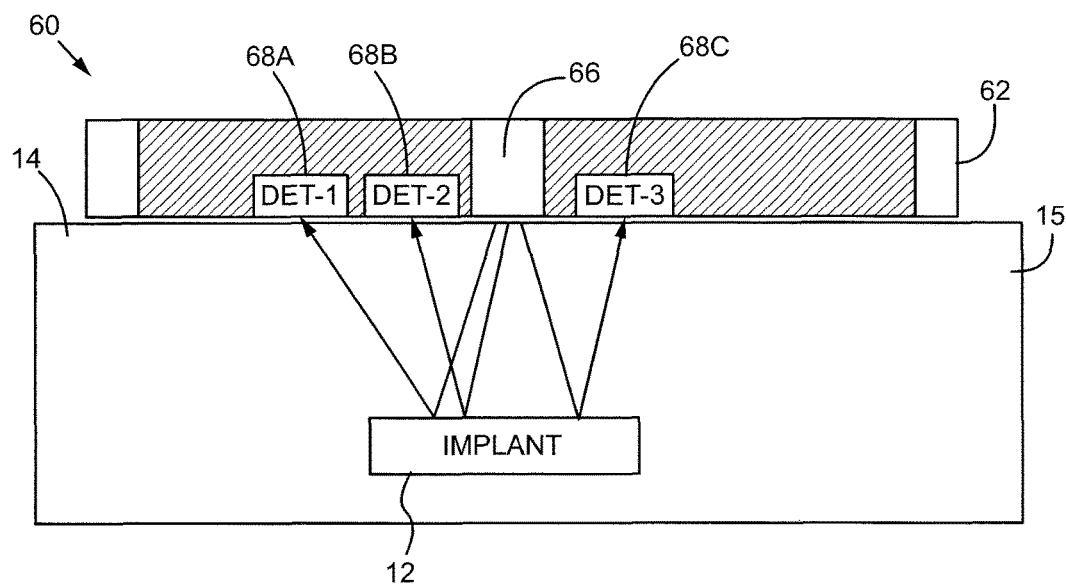
FIG. 6 shows a schematic side view of an optical detection device according to some embodiments of the invention.

As listed in Table 1 and shown in FIG. 4, each of the optical channels 1-3 comprises a respective pairing of one of the three central exciter light sources 64A, 64B, and 64C with a corresponding one of the three central detectors 68A, 68B, and 68C. FIG. 6 shows a schematic side view of the light paths for optical detection of the implant reporters. Excitation light is transmitted through the central via 66 (which preferably contains a monolithic waveguide) from the surface of the skin 14, through the tissue 15, and to the implant 12. Central detectors 68A, 68B, and 68C measure, in response to the excitation light, optical signals emitted from the tissue 15 at the surface of the skin 14 in respective emission wavelength ranges.

A suitable dye for the analyte-dependent signal is Alexa 647 which is responsive to excitation light within an excitation wavelength range of about 600 to 650 nm (excitation peak 647 nm) and within an emission wavelength range of about 670 to 750 nm with an emission peak of about 680 nm. A suitable dye for the analyte-independent signal is Alexa 750 which is responsive to excitation light within an excitation wavelength range of about 700 to 760 nm (excitation peak 750 nm) and within an emission wavelength range of about 770 to 850 nm with an emission peak of about 780 nm. A suitable stable reference dye is erbium with a first excitation light wavelength range of about 650 to 670 nm (excitation peak about 650 nm), a second excitation wavelength range of about 800 to 815 nm (with an excitation peak of about 805 nm), and an emission wavelength range of about 980 to 1050 nm (emission peak of about 1020 nm). In another embodiment, erbium an Alexa 647 may be excited from the same light source, which has the advantage that an optional step of power normalization between multiple light sources is reduced or eliminated.

Referring again to Table 1, optical channels 4-6 provide exciter power normalization signals, which are preferred in embodiments where more than one light source is used. The exciter power normalization signals are used to normalize differences in the power of excitation light output by each light source, which output power may vary slightly for each light source. As shown in FIGS. 4-5, the attenuation of excitation light traveling from central via 66 to outer ring 70 is measured, reducing or eliminating contribution by reporters (e.g., fluorophores) of the implant 12. The optical channels 4-6 comprise three combinations of pairings of the three central exciter light sources 64A, 64B, and 64C with outer-ring detector 6. Alternatively, multiple detectors may be used to detect the intensity of exciter power normalization signals, preferably outer-ring detectors. For exciter power normalization signals, excitation light within the excitation wavelength range of an implant reporter is transmitted into the tissue 15. An optical signal emitted from the tissue 15 within the excitation wavelength range is measured by the detector 6. The corrected signal value for an implant reporter may be normalized for exciter power of a respective light source, e.g., by dividing the optical signal measured for the reporter by the measured intensity of the excitation light within the excitation wavelength range.

Figure 7:
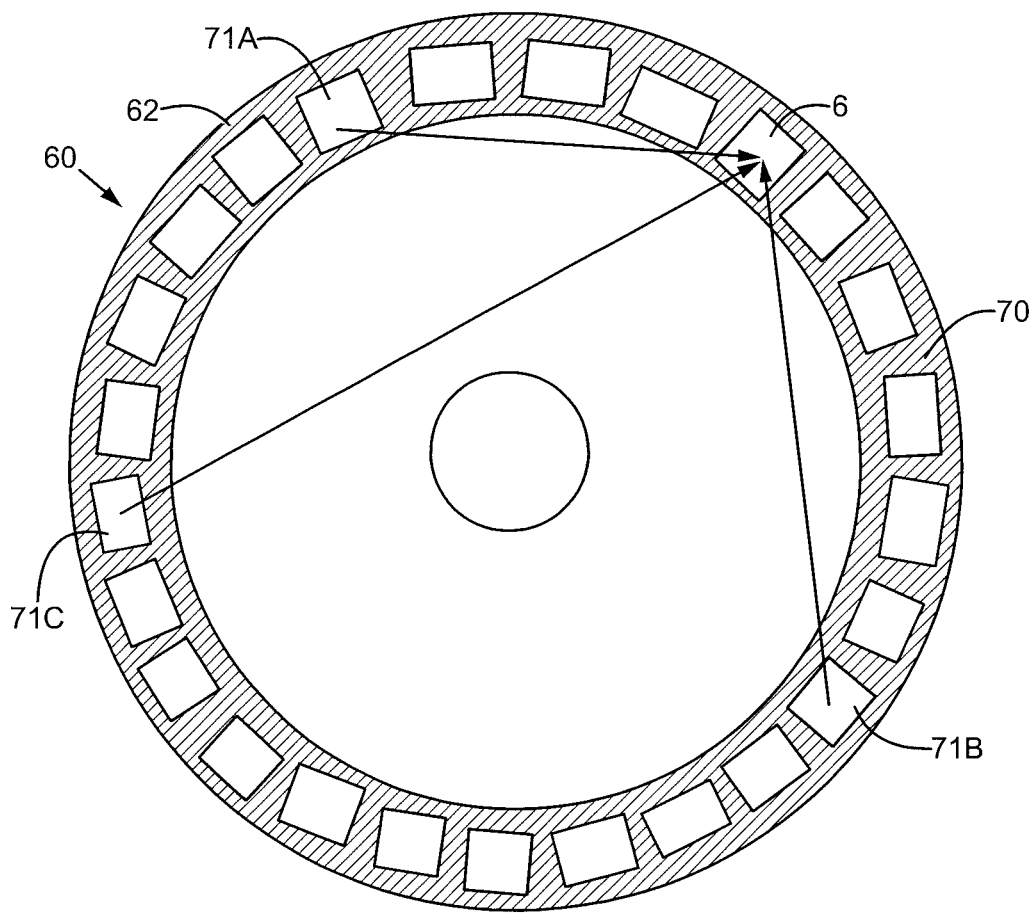
FIG. 7 shows a schematic plan view of an optical detection device according to some embodiments of the invention.
Figure 8:
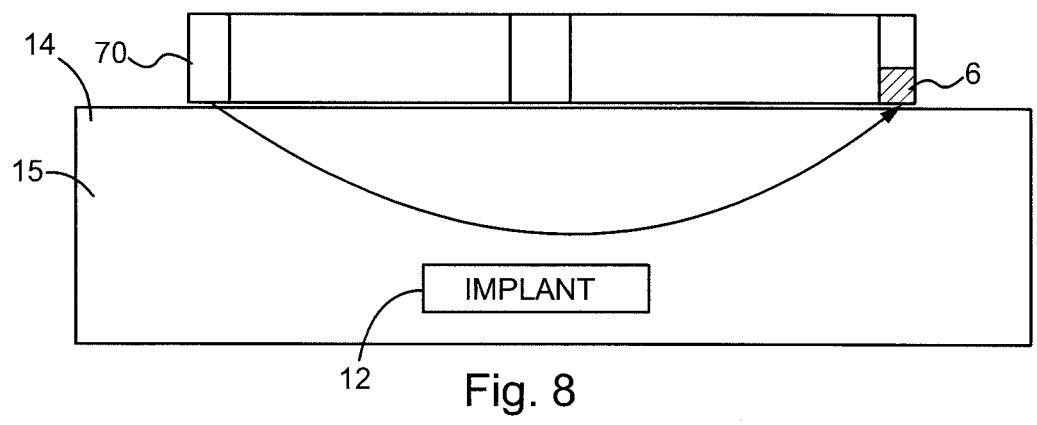
FIG. 8 shows a schematic cross-sectional view of the device of FIG. 7.

Optical channels 7-9 (Table 1) provide diffuse reflectance measurements to correct the luminescent dye reporter signals from the implant. As shown in FIGS. 7-8, outer detector 6 measures attenuation by tissue 15 of light signals in the emission wavelength ranges of the luminescent reporter dyes of the implant 12. Optical channels 7-9 comprise three of the outer exciter light sources 71A, 71B, and 71C arranged in outside ring 70, each paired with the detector 6 in this example, and preferably positioned to provide a range of distances between each light source/detector combination, to compute diffuse reflectance correction values for each luminescent reporter dye of the implant 12. Rather than employing the detector 6 to measure all three optical signals, multiple detectors may be used in alternative embodiments.

Figure 9:
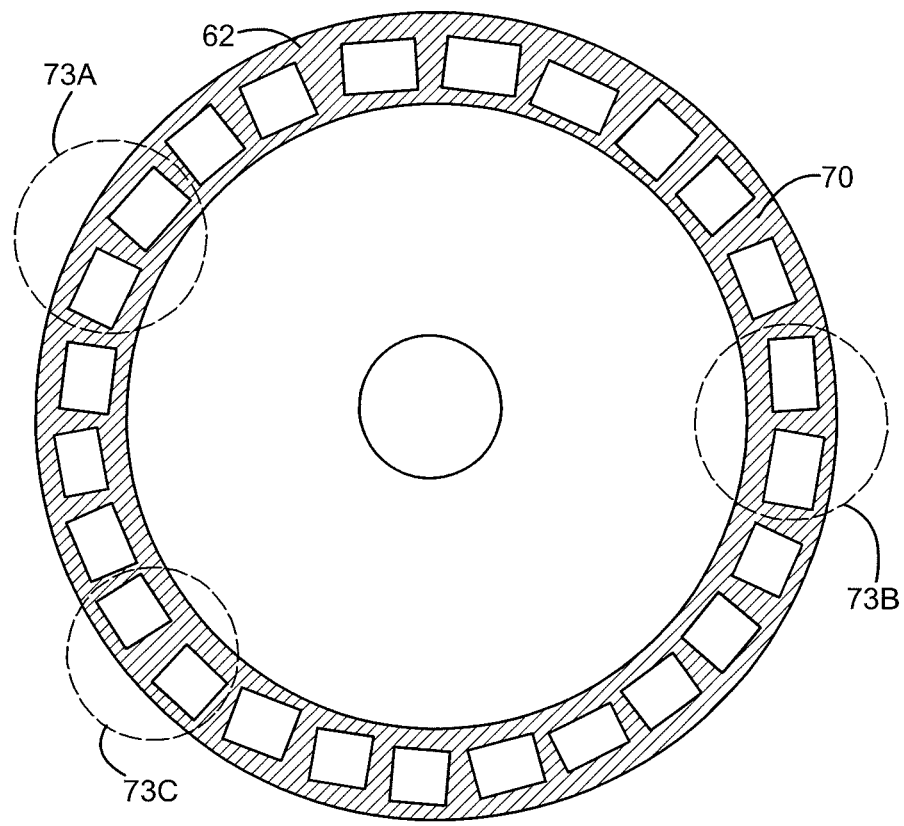
FIG. 9 shows a schematic plan view of an optical detection device according to some embodiments of the invention.
Figure 10:
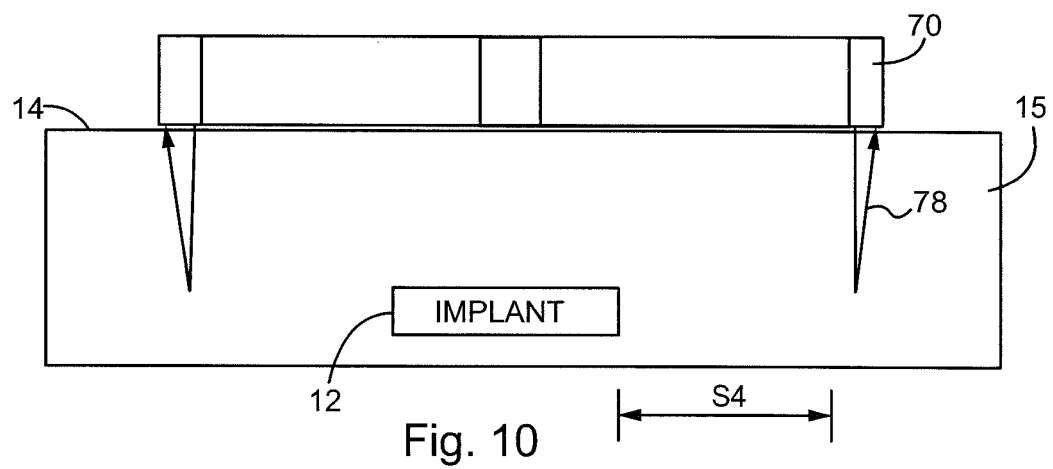
FIG. 10 shows a schematic cross-sectional view of the device of FIG. 9.

Optical channels 10-12 (Table 1) provide measurements of autofluorescence and ambient light to correct the luminescent dye reporter signals from the implant. As shown in FIGS. 9-10, optical channels 10-12 comprise three pairs 73A, 73B, and 73C of the outer exciter light sources and outer-ring detectors arranged in the outside ring 70. The three pairs 73A, 73B, and 73C of the outer exciter light sources and outer detectors provide the same excitation and emission spectra of the three reporter luminescent dyes of the implant 12, and are located on outer ring 70 away from implant 12. In particular, each pair of outer exciter light source/detector for the autofluorescence measurement(s) are positioned with respect to each other such that the excitation light and the light emitted in response to the excitation light form a light path 78 that is spaced laterally from the implant 12 a sufficient distance to avoid significant contribution from implant fluorophores.

It is preferred that the lateral spacing S4 be greater than or equal to 0.25 cm, more preferably greater than 0.5 cm, and most preferably greater than 1 cm. It is also preferred that the depth of the light path 78 extend about 1 to 5 mm into the tissue 15 under the surface of the skin 14. When multiple pairs are used, each light path may have substantially the same depth or different depths, and the measured intensities of the autofluorescence optical signals may be averaged to obtain a correction factor. It is preferred that the contribution from the implant reporter(s) (e.g., fluorophores) to the autofluorescence measurement be less than 30% of the measured intensity, more preferably less than 20%, an most preferably less than 10%.

Figure 11:
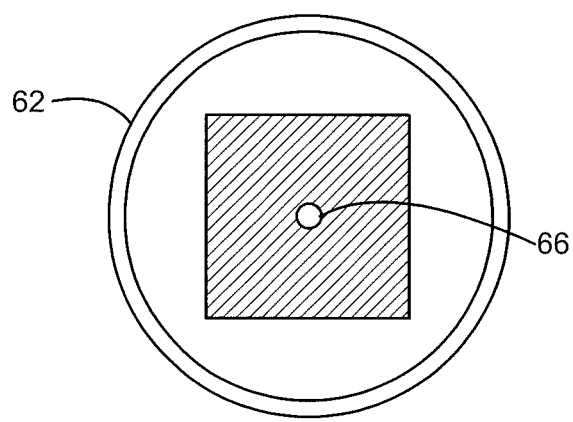
FIG. 11 shows a schematic plan view of an optical detection device according to some embodiments of the invention.
Figure 12:
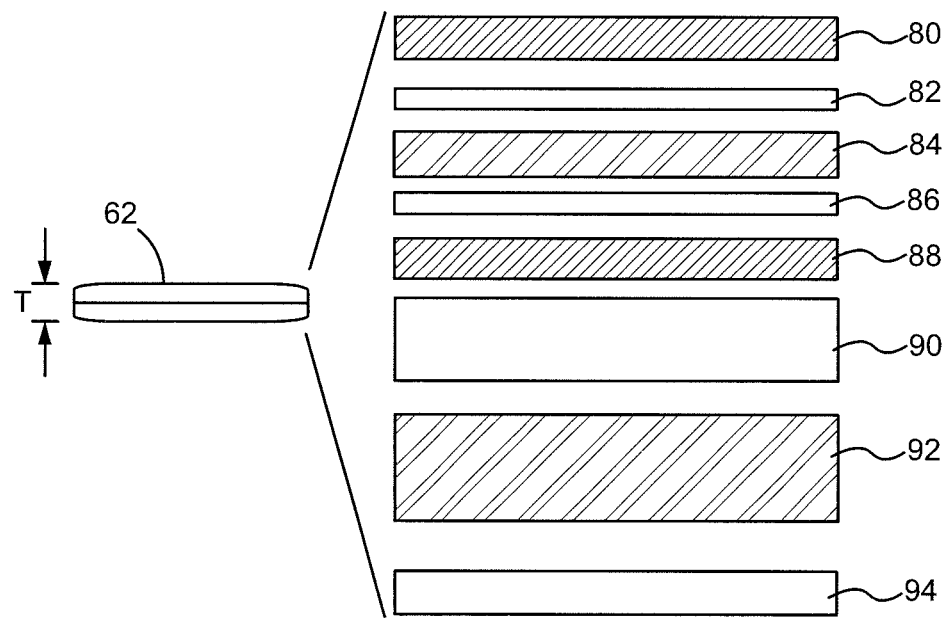
FIG. 12 shows a schematic, exploded view of the device of FIG. 11.

FIG. 11 shows a plan view of the sensor patch 62 having central via 66 for excitation light. Preferred dimensions of patch 62 may be, for example, a diameter of about 16 mm and a thickness T of about 1.6 mm. FIG. 12 shows a schematic, exploded view of the patch 62 comprising multiple layers in a stack. In some embodiments, the layers may comprise a plastic cover 80 having a preferred thickness of about 200 um, a light control film 82 having a preferred thickness of about 100 um, a filter 84 having a preferred thickness of about 200 um, another light control film 86 having a preferred thickness of about 100 um, a silicon layer 88 having a preferred thickness of about 200 um, a printed circuit board (PCB) 90 having a preferred thickness of about 400 um, a battery 92 having a preferred thickness of about 300 um, and a case 94 having a thickness of about 200 um. The PCB 90 may include a microprocessor that is programmed to store measured values and/or to calculate the corrected signal values as previously described. The light control film is a lens array with an aperture array on its back side.

It should be clear to one skilled in the art that embodiments of the described invention may include cabled or wireless hand-held readers, wireless skin patch readers, bench-top instruments, imaging systems, handheld devices (e.g., cell phones or mobile communication devices), smartphone attachments and applications, or any other configuration that utilizes the disclosed optics and algorithms.

Tissue optical heterogeneity in some cases may be significant. Thus, it may be advantageous to utilize a single light source and a single detector to assure that every color passes through the same optical pathway through the tissue. In one embodiment, a light source can be positioned with a set of moveable filters between the light source and the surface of the skin. Similarly a single photodetector can be utilized in place of separate discrete detector elements. The detector may be used to detect different colors by using moveable or changeable filters to enable multiple wavelengths to be measured. Changing or moving filters may be accomplished by a mechanical actuator controlling a rotating disc, filter strip or other means. Alternatively, optical filters may be coated with a material that when subjected to current, potential, temperature or another controllable influence, will change optical filtering properties, so that a single photodetector can serve to detect multiple colors.

It will be clear to one skilled in the art that the above embodiments may be altered in many ways without departing from the scope of the invention. For example, many different permutations or arrangements of one or more light sources, one or more detectors, filters, and/or fibers connecting the optical components may be used to realize the device and method of the invention. For example, in some embodiments the light sources and detectors are arranged with optical fibers or cables to transmit excitation light into the skin and measure optical signals emitted from the skin, without having to position the light sources and detectors directly on the skin of an individual. Presently preferred values for dimensions of the device and/or wavelength ranges may differ in alternative embodiments. Accordingly, the scope of the invention should be determined by the following claims and their legal equivalents.

What is claimed is:

1. A device, comprising:
   a sensor patch configured to be placed on a surface of a skin of a mammalian body, the sensor patch including a case;
   a first light source disposed within the case and located within a center portion of the case, the first light source pre-configured to generate a first optical signal within an excitation wavelength range of a luminescent dye to illuminate an implant containing the luminescent dye embedded in tissue of the mammalian body, the luminescent dye configured to emit an analyte-dependent optical signal within an emission wavelength range in response to absorbing light within the excitation wavelength range;
   a second light source disposed within the case and located within the center portion of the case, the second light source pre-configured to generate a second optical signal within the emission wavelength range to illuminate the tissue; and
   a plurality of detectors disposed within the case and in a ring configuration around the central portion of the case, a first detector from the plurality of detectors configured to (1) receive a third optical signal emitted from the implant embedded in the tissue, the third optical signal being within the emission wavelength range and emitted by the implant in response to the implant being illuminated with the first optical signal and (2) receive a fourth optical signal in response to the tissue being illuminated by the second optical signal, the fourth optical signal being within the emission wavelength range.

2. The device of claim 1, further comprising at least one processor disposed within the case configured to:
   receive data from the first detector representative of the third optical signal indicative of a concentration of the analyte and data representative of the fourth optical signal indicative of at least one of diffuse reflectance or scattering of light in the tissue,
   calculate a correction factor using the data representative of the third optical signal and the data representative of the fourth optical signal, and
   calculate at least one of a quantity or a concentration of analyte by applying the correction factor to the data representative of the third optical signal.

3. The device of claim 1, wherein a distance between the second light source and the first detector within the case is substantially equal to a distance between the first light source and the first detector within the case such that the first optical signal and the second optical signal each travel a light path that extends to a depth in the tissue that is substantially equal to a depth at which the implant is embedded.

4. The device of claim 1, wherein a distance between the second light source and the first detector within the case is greater than a distance between the first light source and the first detector within the case such that the second optical signal travels a light path that extends to a depth in the tissue that is greater than a depth at which the implant is embedded.

5. The device of claim 1, wherein the second light source is spaced apart from the first detector within the case such that the second optical signal travels a light path that extends to a depth of 1 to 5 mm under a surface of skin.

6. The device of claim 1, wherein the implant is embedded in subcutaneous tissue, and the second light source and a second detector from the plurality of detectors are configured such that the second optical signal travels a light path that extends to a depth in the tissue greater than or equal to 3 mm under a surface of skin.

7. The device of claim 1, wherein the first detector and the second light source spaced a first distance apart within the case such that the second optical signal and the fourth optical signal collectively define a first light path that extends to a first depth in the tissue, and the implant is embedded at a second depth in the tissue, the device further comprising:
 a third light source disposed within the case and configured to generate a fifth optical signal to illuminate the tissue; and
 a second detector disposed within the case and configured to receive a sixth optical signal emitted from the tissue, the third light source and the second detector spaced apart within the case a second distance different from the first distance such that the fifth optical signal and the sixth optical signal collectively define a second light path that extends to a third depth in the tissue, the second depth differing from the first depth and the third depth.

8. The device of claim 1, wherein the implant is embedded at a first depth in the tissue, the second light source and a second detector from the plurality of detectors are collectively configured such that the second optical signal travels a light path that extends to a second depth in the tissue, the device further comprising:
 a processor disposed within the case configured to:
  receive data representative of an analyte-independent optical signal emitted from the implant, and
  determine the second depth using the data representative of the analyte-independent signal.

9. The device of claim 2, wherein the processor is further configured to:
 receive data representative of an analyte-independent optical signal emitted from the implant, and
 calculate the correction factor using the data representative of an analyte-independent optical signal.

10. The device of claim 1, wherein:
 the analyte-dependent optical signal is a first analyte-dependent optical signal;
 the emission wavelength range is a first emission wavelength range;
 the excitation wavelength range is a first excitation wavelength range;
 the luminescent dye is a first luminescent dye configured to emit the first analyte-dependent optical signal within the first emission wavelength range in response to absorbing light within the first excitation wavelength range;

the implant includes a second luminescent dye configured to emit an analyte-independent optical signal within a second emission wavelength range in response to absorbing light within a second excitation wavelength range, the device further comprising:
 a third light source disposed within the case and pre-configured generate a fifth optical signal within the second excitation wavelength range to illuminate the implant, a second detector from the plurality of detectors configured to receive a sixth optical signal emitted from the implant, the sixth optical signal being within the second emission wavelength range and emitted from the implant in response to the implant being illuminated with the fifth optical signal; and
 a fourth light source disposed within the case and pre-configured to generate a seventh optical signal within the second emission wavelength range to illuminate the tissue, the second detector configured to receive an eighth optical signal in response to the tissue being illuminated by the seventh optical signal.

11. The device of claim 2, wherein:
 a second detector from the plurality of detectors is further configured to receive a fifth optical signal in response to the tissue being illuminated by a sixth optical signal, the sixth optical signal within the excitation wavelength range; and
 the processor is further configured to calculate the correction factor using data representative of the fifth optical signal.

12. The device of claim 1, wherein the first light source and the second light source are light emitting diodes.

13. A device, comprising:
 a case;
 a plurality of light sources and a detectors disposed within the case, each detector from the plurality of detectors disposed adjacent to a light source from the plurality of light sources in a ring configuration in an outer ring portion of the case;
 a first light source from the plurality of light sources disposed within a first portion of the case and pre-configured to generate a first optical signal within a first excitation wavelength range to illuminate an implant embedded in tissue of a mammalian body, the implant configured to emit an analyte-dependent optical signal within a first emission wavelength range in response to absorbing light within the first excitation wavelength range, the first emission wavelength range being different from the first excitation wavelength range, the implant configured to emit an analyte-independent optical signal within a second emission wavelength range in response to absorbing light within a second excitation wavelength range;
 a first detector from the plurality of detectors disposed within the first portion of the case and configured to receive a second optical signal emitted from the implant in response to the implant being illuminated with the first optical signal, the second optical signal being within the first emission wavelength range;
 a second light source from the plurality of light sources and pre-configured to generate a third optical signal to illuminate the implant with the second excitation wavelength range; and
 a second detector from the plurality of detectors disposed within a second portion of the case and configured to receive a fourth optical signal emitted from the implant embedded in the tissue, the fourth optical signal being within a second emission wavelength range, the fourth optical signal emitted by the implant in response to the implant being illuminated with the third optical signal, the second portion of the case being mutually exclusive such that the first optical signal and the second optical signal define a first light path that is spaced laterally apart from a second light path defined by the third optical signal and the fourth optical signal.

14. The device of claim 13, further comprising:
a printed circuit board disposed within the case, the first detector and at least one processor disposed on the printed circuit board, the at least one processor configured to:
receive data representative of the second optical signal indicative of a concentration of the analyte and data representative of the fourth optical signal,
calculate a correction factor using the data representative of the second optical signal and the data representative of the fourth optical signal, and
calculate at least one of a quantity or a concentration of the analyte by applying the correction factor to the data representative of the second optical signal.

15. The device of claim 13, further comprising:
a third light source from the plurality of light sources pre-configured to generate a fifth optical signal within the first excitation wavelength range to illuminate the tissue within the first excitation wavelength range; and
a third detector from the plurality of detectors configured to receive a seventh optical signal emitted from the tissue, the seventh optical signal indicative of autofluorescence and emitted from the tissue in response to the tissue being illuminated with the fifth optical signal.

16. The device of claim 13, further comprising:
a third detector from the plurality of detectors configured to receive a fifth optical signal; and
at least one processor disposed within the case and configured to:
receive data representative of the second optical signal indicative of a concentration of the analyte and data representative of the fifth optical signal indicative of light reflected from the tissue within the first excitation wavelength range,
calculate a correction factor using the data representative of the second optical signal and the data representative of the fifth optical signal, and
calculate at least one of a quantity or a concentration of the analyte by applying the correction factor to the data representative of the second optical signal.

17. The device of claim 13, further comprising:
a third light source from the plurality of light sources configured to generate a fifth optical signal to illuminate the tissue; and
a third detector from the plurality of detectors disposed within a third portion of case and configured to receive a sixth optical signal emitted from the tissue in response to the tissue being illuminated with the fifth optical signal, the first portion of the case and the third portion of the case mutually exclusive such that the fifth optical signal and the sixth optical signal form a third light path that is spaced laterally from the implant when the first light source illuminates the implant such that the sixth optical signal does not include a significant contribution from the implant.

18. The device of claim 1, wherein:
the first light source is positioned to transmit the first generated light through a central via in the sensor patch.

19. The device of claim 1, wherein the excitation wavelength range and the emission wavelength range are mutually exclusive.

20. The device of claim 1, wherein:
the excitation wavelength range is 600 to 650 nm; and
the emission wavelength range is 670 to 750 nm.

21. The device of claim 1, further comprising:
a third light source disposed within the case and in the ring configuration in an outer ring portion of the case.

22. The device of claim 1, wherein:
the plurality of detectors is a first plurality of detectors; and
a third light source and a second plurality of detectors are disposed in a second ring configuration in an outer ring portion of the case outside the first ring configuration.

23. The device of claim 21, wherein:
the first light source is located in the center portion of the case and spaced apart from the outer ring portion of the case by at least 1 cm.

24. A device, comprising:
a sensor patch configured to be placed on a surface of a skin of a mammalian body, the sensor patch including a case;
a first light source from a plurality of light sources disposed within the case, the first light source pre-configured to generate a first optical signal within an excitation wavelength range of a luminescent dye to illuminate an implant containing the luminescent dye embedded in tissue of the mammalian body, the luminescent dye configured to emit an analyte-dependent optical signal within an emission wavelength range in response to absorbing light within the excitation wavelength range;
a second light source from the plurality of light sources disposed within the case, the second light source pre-configured to generate a second optical signal within the emission wavelength range to illuminate the tissue; and
a plurality of detectors disposed within the case each detector from the plurality of detectors disposed adjacent to a light source from the plurality of light sources in a ring configuration in an outer ring portion of the case, a first detector from the plurality of detectors configured to (1) receive a third optical signal emitted from the implant embedded in the tissue, the third optical signal being within the emission wavelength range and emitted by the implant in response to the implant being illuminated with the first optical signal and (2) receive a fourth optical signal in response to the tissue being illuminated by the second optical signal, the fourth optical signal being within the emission wavelength range.

25. The device of claim 24, wherein the first detector and the first light source are disposed within a first portion of the case such that the first optical signal and the third optical signal travels a first light path that includes the implant and is associated with the first portion of the case, the device further comprising:
a third light source disposed within a second portion of the case, the third light source pre-configured to generate a fifth optical signal within the excitation wavelength range to illuminate the tissue; and
a second detector disposed within the second portion of the case, the second detector configured to receive a sixth optical signal emitted from the tissue, the sixth optical signal being within the emission wavelength range, the first portion of the case mutually exclusive from the first portion of the case such that the fifth optical signal and the sixth optical signal travel a second light path associated with the second portion of the case that is spaced laterally from the implant when the first light source illuminates the implant such that the sixth optical signal does not include a significant contribution from the implant.

26. A device, comprising:

a case;

a first light source disposed within a center portion of the case and pre-configured to generate a first optical signal within a first excitation wavelength range to illuminate an implant embedded in tissue of a mammalian body, the implant configured to emit an analyte-dependent optical signal within a first emission wavelength range in response to absorbing light within the first excitation wavelength range, the first emission wavelength range being different from the first excitation wavelength range, the implant configured to emit an analyte-independent optical signal within a second emission wavelength range in response to absorbing light within a second excitation wavelength range;

a plurality of detectors disposed within the case in a ring configuration around the central portion of the case;

a first detector from the plurality of detectors disposed within the first portion of the case and configured to receive a second optical signal emitted from the implant in response to the implant being illuminated with the first optical signal, the second optical signal being within the first emission wavelength range;

a second light source disposed within the case and pre-configured to generate a third optical signal to illuminate the implant with the second excitation wavelength range; and a second detector from the plurality of detectors disposed within a second portion of the case and configured to receive a fourth optical signal emitted from the implant embedded in the tissue, the fourth optical signal being within a second emission wavelength range, the fourth optical signal emitted by the implant in response to the implant being illuminated with the third optical signal, the second portion of the case being mutually exclusive such that the first optical signal and the second optical signal define a first light path that is spaced laterally apart from a second light path defined by the third optical signal and the fourth optical signal.

27. The device of claim 13, wherein:

a first subset of the plurality of detectors, including the first detector, is disposed in a first ring configuration around the central portion of the case; and the second light source and a second subset of the plurality of detectors, including the second detector, are disposed in a second ring configuration in an outer ring portion of the case outside of the first ring configuration.

28. The device of claim 13, wherein the second light source is disposed in an outer ring portion of the case.

29. The device of claim 28, wherein:

the center portion of the case is spaced apart from the outer ring portion of the case by at least 1 cm.

* * * * *

UNITED STATES PATENT AND TRADEMARK OFFICE
CERTIFICATE OF CORRECTION

PATENT NO. : 10,045,722 B2
APPLICATION NO. : 14/199497
DATED : August 14, 2018
INVENTOR(S) : Gregory J. Kintz et al.

Page 1 of 1

It is certified that error appears in the above-identified patent and that said Letters Patent is hereby corrected as shown below:

In the Specification

At Column 1, Line number 13, please add the following:
-- STATEMENT REGARDING FEDERALLY SPONSORED RESEARCH OR DEVELOPMENT
This invention was made with government support under grant numbers NIH R01 EB016414 and NIH R43 DK093139, awarded by the National Institutes of Health. The government has certain rights in the invention--.

Signed and Sealed this
Thirtieth Day of October, 2018

Andrei Iancu
*Director of the United States Patent and Trademark Office*